United States Patent
Sing et al.

(10) Patent No.: US 7,037,322 B1
(45) Date of Patent: May 2, 2006

(54) SYSTEM AND METHOD FOR DELIVERING HEMOSTASIS PROMOTING MATERIAL TO A BLOOD VESSEL PUNCTURE WITH A STAGING TUBE

(75) Inventors: Eduardo Chi Sing, Dana Point, CA (US); Mark Ashby, Laugna Niguel, CA (US); Luis R. Urquidi, Laguna Hills, CA (US)

(73) Assignee: Sub-Q, Inc., San Clemente, CA (US)

( * ) Notice: Subject to any disclaimer, the term of this patent is extended or adjusted under 35 U.S.C. 154(b) by 0 days.

(21) Appl. No.: 10/461,006

(22) Filed: Jun. 13, 2003

Related U.S. Application Data

(63) Continuation-in-part of application No. 10/007,204, filed on Nov. 8, 2001, and a continuation-in-part of application No. 10/256,493, filed on Sep. 26, 2002.

(51) Int. Cl.
*A61B 17/08* (2006.01)

(52) U.S. Cl. ..................................................... 606/213

(58) Field of Classification Search ................ 606/213, 606/215, 216, 228–231; 604/11, 13, 15, 604/60, 131, 116, 117, 168.01, 500, 158, 604/159

See application file for complete search history.

(56) References Cited

U.S. PATENT DOCUMENTS

| 581,235 | A | 4/1897 | Kenyon |
|---|---|---|---|
| 1,578,517 | A | 3/1926 | Hein |
| 2,086,580 | A | 7/1937 | Shirley |
| 2,465,357 | A | 3/1949 | Correll |
| 2,492,458 | A | 12/1949 | Bering, Jr. |
| 2,507,244 | A | 5/1950 | Correll |
| 2,558,395 | A | 6/1951 | Studer |
| 2,597,011 | A | 5/1952 | MacMasters et al. |
| 2,680,442 | A | 6/1954 | Linzmayer |
| 2,761,446 | A | 9/1956 | Reed |
| 2,814,294 | A | 11/1957 | Figge |
| 2,824,092 | A | 2/1958 | Thompson |
| 2,899,362 | A | 8/1959 | Sieger, Jr., et al. |
| 3,157,524 | A | 11/1964 | Artandi |
| 3,703,174 | A | * | 11/1972 | Smith ......................... 604/159 |

(Continued)

FOREIGN PATENT DOCUMENTS

EP 0032826 7/1981

(Continued)

OTHER PUBLICATIONS

Allison, D., et al., "Percutaneous liver biopsy and track embolization with steel coils", Radiology, vol. 169, pp. 261-263, (1998).

(Continued)

*Primary Examiner*—Sharon Kennedy
(74) *Attorney, Agent, or Firm*—Miller, Matthias & Hull

(57) ABSTRACT

A system for delivering hemostasis promoting material of the present invention allows the hemostasis promoting material to be delivered to a blood vessel puncture site by fluid pressure. The system allows the hemostasis promoting material to be delivered through an introducer sheath which is already in place within a tissue tract. This system includes a controlled tip which is insertable through the introducer sheath to locate and occlude the blood vessel puncture site and a hydration chamber for receiving and delivering the hemostasis promoting material to the blood vessel puncture site. The system accurately locates the blood vessel wall at a puncture site and for properly placing a hemostasis plug over the puncture site.

10 Claims, 34 Drawing Sheets

U.S. PATENT DOCUMENTS

| | | | |
|---|---|---|---|
| 3,724,465 A | 4/1973 | Duchane | |
| 4,000,741 A | 1/1977 | Binard et al. | |
| 4,211,323 A | 7/1980 | Olsen | |
| 4,218,155 A | 8/1980 | Weidner | |
| 4,238,480 A | 12/1980 | Sawyer | |
| 4,292,972 A | 10/1981 | Pawelchak | |
| 4,323,072 A | 4/1982 | Rosenbluth et al. | |
| 4,340,066 A | 7/1982 | Shah | |
| 4,390,018 A | 6/1983 | Zuloowski | |
| 4,404,970 A | 9/1983 | Sawyer | |
| 4,515,637 A | 5/1985 | Cioca | |
| 4,573,576 A | 3/1986 | Krol | |
| 4,587,969 A | 5/1986 | Gillis | |
| 4,588,395 A | 5/1986 | Lemelson | |
| 4,619,261 A | 10/1986 | Guerriero | |
| 4,619,913 A | 10/1986 | Luck et al. | |
| 4,645,488 A | 2/1987 | Matukas | |
| 4,708,718 A | 11/1987 | Daniels | |
| 4,744,364 A | 5/1988 | Kensey | |
| 4,790,819 A | 12/1988 | Li et al. | |
| 4,829,994 A | 5/1989 | Kurth | |
| 4,850,960 A | 7/1989 | Grayzel | |
| 4,852,568 A | 8/1989 | Kensey | |
| 4,890,612 A | 1/1990 | Kensey | |
| 4,900,303 A | 2/1990 | Lemelson | |
| 4,929,246 A | 5/1990 | Sinofsky | |
| 4,936,835 A | 6/1990 | Haaga | |
| 4,950,234 A | 8/1990 | Fujioka et al. | |
| 5,007,895 A | 4/1991 | Burnett | |
| 5,021,059 A | 6/1991 | Kensey et al. | |
| 5,053,046 A | 10/1991 | Janese | |
| 5,061,274 A | 10/1991 | Kensey | |
| 5,080,655 A | 1/1992 | Haaga | |
| 5,106,376 A * | 4/1992 | Mononen et al. | 604/164.11 |
| 5,108,421 A | 4/1992 | Fowler | |
| 5,160,323 A * | 11/1992 | Andrew | 604/158 |
| 5,163,904 A | 11/1992 | Lampropoulos et al. | |
| 5,167,624 A | 12/1992 | Butler et al. | |
| 5,192,300 A | 3/1993 | Fowler | |
| 5,192,301 A | 3/1993 | Kamiya et al. | |
| 5,195,988 A | 3/1993 | Haaga | |
| 5,220,926 A | 6/1993 | Jones | |
| 5,221,259 A | 6/1993 | Weldon et al. | |
| 5,242,683 A | 9/1993 | Klaveness | |
| 5,275,616 A | 1/1994 | Fowler | |
| 5,282,827 A | 2/1994 | Kensey et al. | |
| 5,310,407 A | 5/1994 | Casale | |
| 5,322,515 A | 6/1994 | Karas et al. | |
| 5,325,857 A | 7/1994 | Nabai et al. | |
| 5,334,216 A | 8/1994 | Vidal et al. | |
| 5,366,480 A | 11/1994 | Corriveau et al. | |
| 5,370,656 A | 12/1994 | Shevel | |
| 5,383,896 A | 1/1995 | Gershony et al. | |
| 5,383,899 A | 1/1995 | Hammersiag | |
| 5,385,550 A | 1/1995 | Su et al. | |
| 5,388,588 A | 2/1995 | Nabai et al. | |
| 5,391,183 A | 2/1995 | Janzen et al. | |
| 5,399,361 A | 3/1995 | Song et al. | |
| 5,417,699 A | 5/1995 | Klein | |
| 5,419,765 A | 5/1995 | Weldon et al. | |
| 5,431,639 A | 7/1995 | Shaw | |
| 5,437,292 A | 8/1995 | Kipshidze | |
| 5,437,631 A | 8/1995 | Janzen | |
| 5,443,481 A | 8/1995 | Lee | |
| 5,467,780 A | 11/1995 | Nabai et al. | |
| 5,478,352 A | 12/1995 | Fowler | |
| 5,479,936 A | 1/1996 | Nabai et al. | |
| 5,486,195 A | 1/1996 | Myers | |
| 5,490,736 A | 2/1996 | Haber | |
| 5,522,840 A | 6/1996 | Krajicek | |
| 5,522,850 A | 6/1996 | Yomtov et al. | |
| 5,526,822 A | 6/1996 | Burbank et al. | |
| 5,527,332 A | 6/1996 | Clement | |
| 5,529,577 A | 6/1996 | Hammershiag | |
| 5,540,715 A | 7/1996 | Katsaros et al. | |
| 5,542,914 A | 8/1996 | Van Iten | |
| 5,545,178 A | 8/1996 | Kensey et al. | |
| 5,558,853 A | 9/1996 | Quay | |
| 5,591,204 A | 1/1997 | Janzen et al. | |
| 5,591,205 A | 1/1997 | Fowler | |
| 5,601,602 A | 2/1997 | Fowler | |
| 5,601,603 A | 2/1997 | Illi | |
| 5,645,566 A | 7/1997 | Brennenman et al. | |
| 5,649,547 A | 7/1997 | Ritchart et al. | |
| 5,653,730 A | 8/1997 | Hammersiag | |
| 5,665,107 A | 9/1997 | Hammersiag | |
| 5,676,689 A | 10/1997 | Kensey | |
| 5,681,279 A | 10/1997 | Roper et al. | |
| 5,716,375 A | 2/1998 | Fowler | |
| 5,725,498 A | 3/1998 | Janzen et al. | |
| 5,741,223 A | 4/1998 | Janzen et al. | |
| 5,769,086 A | 6/1998 | Ritchart et al. | |
| 5,775,333 A | 7/1998 | Burbank et al. | |
| 5,782,861 A | 7/1998 | Cragg et al. | |
| 5,800,389 A | 9/1998 | Burney et al. | |
| 5,810,806 A | 9/1998 | Ritchart et al. | |
| 5,830,130 A | 11/1998 | Janzen et al. | |
| 5,858,008 A | 1/1999 | Capaccio | |
| 5,868,762 A | 2/1999 | Cragg et al. | |
| 5,902,310 A | 5/1999 | Foerster et al. | |
| 5,984,950 A | 11/1999 | Cragg et al. | |
| 6,007,563 A | 12/1999 | Nash et al. | |
| 6,027,471 A | 2/2000 | Fallon et al. | |
| 6,027,482 A | 2/2000 | Imbert | |
| 6,045,570 A * | 4/2000 | Epstein et al. | 606/214 |
| 6,071,300 A | 6/2000 | Brenneman et al. | |
| 6,071,301 A | 6/2000 | Cragg et al. | |
| 6,086,607 A | 7/2000 | Cragg et al. | |
| 6,161,034 A | 12/2000 | Burbank et al. | |
| 6,162,192 A | 12/2000 | Cragg et al. | |
| 6,183,497 B1 | 2/2001 | Sing et al. | |
| 6,200,328 B1 | 3/2001 | Cragg et al. | |
| 6,315,753 B1 | 11/2001 | Cragg et al. | |

FOREIGN PATENT DOCUMENTS

| | | |
|---|---|---|
| EP | 0476178 | 3/1992 |
| EP | 0482350 | 4/1992 |
| EP | 0557963 | 2/1993 |
| EP | 0637431 | 11/1994 |
| FR | 2641692 | 7/1990 |
| GB | 1509023 | 4/1978 |
| GB | 1569660 | 6/1980 |
| RU | 782814 | 11/1980 |
| RU | 1088709 A | 4/1984 |
| WO | WO 91/12847 | 9/1991 |
| WO | WO 94/02072 | 2/1994 |
| WO | WO 94/28800 | 12/1994 |
| WO | WO 95/28124 | 10/1995 |
| WO | WO 95/32669 | 12/1995 |
| WO | WO 95/32671 | 12/1995 |
| WO | WO 96/08208 | 3/1996 |
| WO | WO 96/24290 | 8/1996 |
| WO | WO 98/06346 | 2/1998 |
| WO | WO 99/66834 | 12/1999 |

OTHER PUBLICATIONS

J. Bryne Review Article: Endovasular treatments for intracranial anuerysms, 1996 The British journal of radiology; 98,891-899.

Chunag, V., et al., "Sheath needle for liver biopsy in high-risk patience", Radiology, vol. 166, pp. 261-262 (1988).

John T. Correll, et al., A new Physiologically absorbable sponge.

John T. Correll, et al. Biologic investigations of new absorbable sponge; p. 585.

Fandrich, C., et al. "Small guage gelfoam plug liver biopsy in high risk patients", Australian Radiology, vol. 40, pp. 230-234 (1996).

Foran, JPM, et al. "Early mobilisation after percutaneous cardiac catheterisation using collagen plug (vasoseal) maemostatis" BRHeart, vol. 69, pp. 424-429 (1993).

Gibbs, JSR, "Femoral arterial hemostasis" J. Interventional card, vol. 5, pp. 85-88 (1992).

Journal of interventional cardiology vol. 5 No. 2 Jun.

Kassell, et al. Size of Intracanial aneurysm; vol. 12, No. 3, (1983).

Kiemeneiji, F, et al., "Improved anticoagulation management after Palmaz Schatz coronary stent implantation by sealing the arterial puncture site with vascular hemostasis device", Catheterization and Cardiovascular diagnosis, vol. 30, pp. 1685-1692 (1995).

Kussmaul, WG, "Rapid arterial hemostasis", J. Am. Coll. Card., vol. 25, pp. 1685-1692 (1995).

Pharmacia & Upjohn manufacturer brochure gelfoam sterile sponge, sterile powder and sterile film, pp. 1-34 (May 1997).

Pharmacia & Upjohn manufacturer brochure gelfoam sterile powder, (Feb. 1996).

Pharmacia & Upjohn manufacturer brochure, "gelfoam sterile powder" (Mar. 1996).

Pharmacia & Upjohn manufacturer brochure (Sep. 1996).

Pharmacia & Upjohn maufacturer specification, "Gelfoam sterile sponge, sterile powder and sterile film" pp. 1-23 (Nov. 1996).

Riley, SA, Percutaneous liver biopsy with plugging of needle track: a safe method for use in patients with impaired coagulation, The lancet, p. 436 (1964).

Sanborn, T. Multicenter randomized trial comparing perutaneous collagen hemostasis device with conventional manual compression after diagnostic angiography and angioplasty, J. Am. Coll. Card., vol. 22, pp. 1273-1279, (1993).

Schievink, et al. The new england journal of medicame; review articles; intracinal aneurysms; Jan. 2, 1997.

Scharader, R. "Collagen appl.", Catheterization & cardiovascular diagnosis (1992) pp. 298-302.

Silber, S., "Rapid hemostasis of arterial puncture sites with collagen in patients undergoing diagnostic interventional cardiac catherterization", clinical cardiology, vol. 20, pp. 981-992, (1997).

Smith, T., "Percutanous transhepatic liver biopsy with tract embolization", Radiology, vol. 198, pp. 769-774 (1996).

Szikora, et al. Combined Use of stents and cells to treat experimental wide-necked carotid aneuryms: Preliminary results; AJNR AM newradiol 15: 1091-1102, Jun. 1994.

Szikora, et al. Endovascular treatment of experimental anuerysms with liquid polymers: vol. 38, No. 2, Feb. 1996.

Turjman, et al. Combined stent implantation & endosacular coil placement for treatment of experimental wide-necked aneurysms:AJNRAM J. Neuroradio 15: 1087-1090 Jun. 1994.

Yoshimoto, et al cerebral anuerysms unrelated to arterial bifurcations; Acta neurochir (Wien) (96) 138: 958-964.

Zins, M., "US-guided percutaneous liver biopsy with plugging of the needle track" radiology, vol. 187, pp. 841-843, (1992).

* cited by examiner

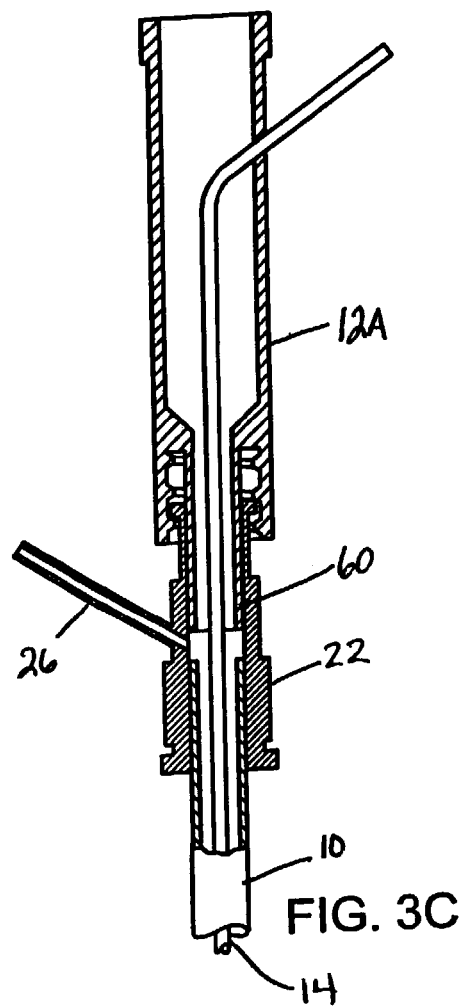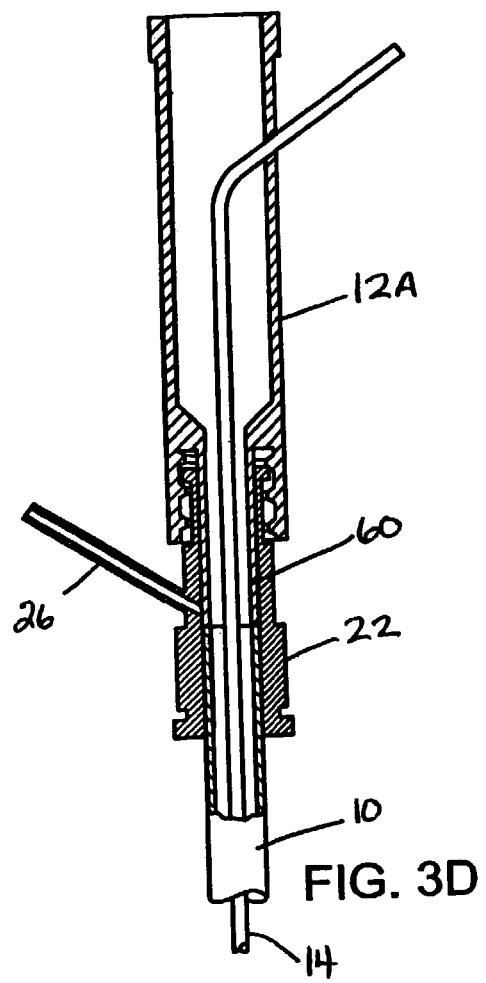

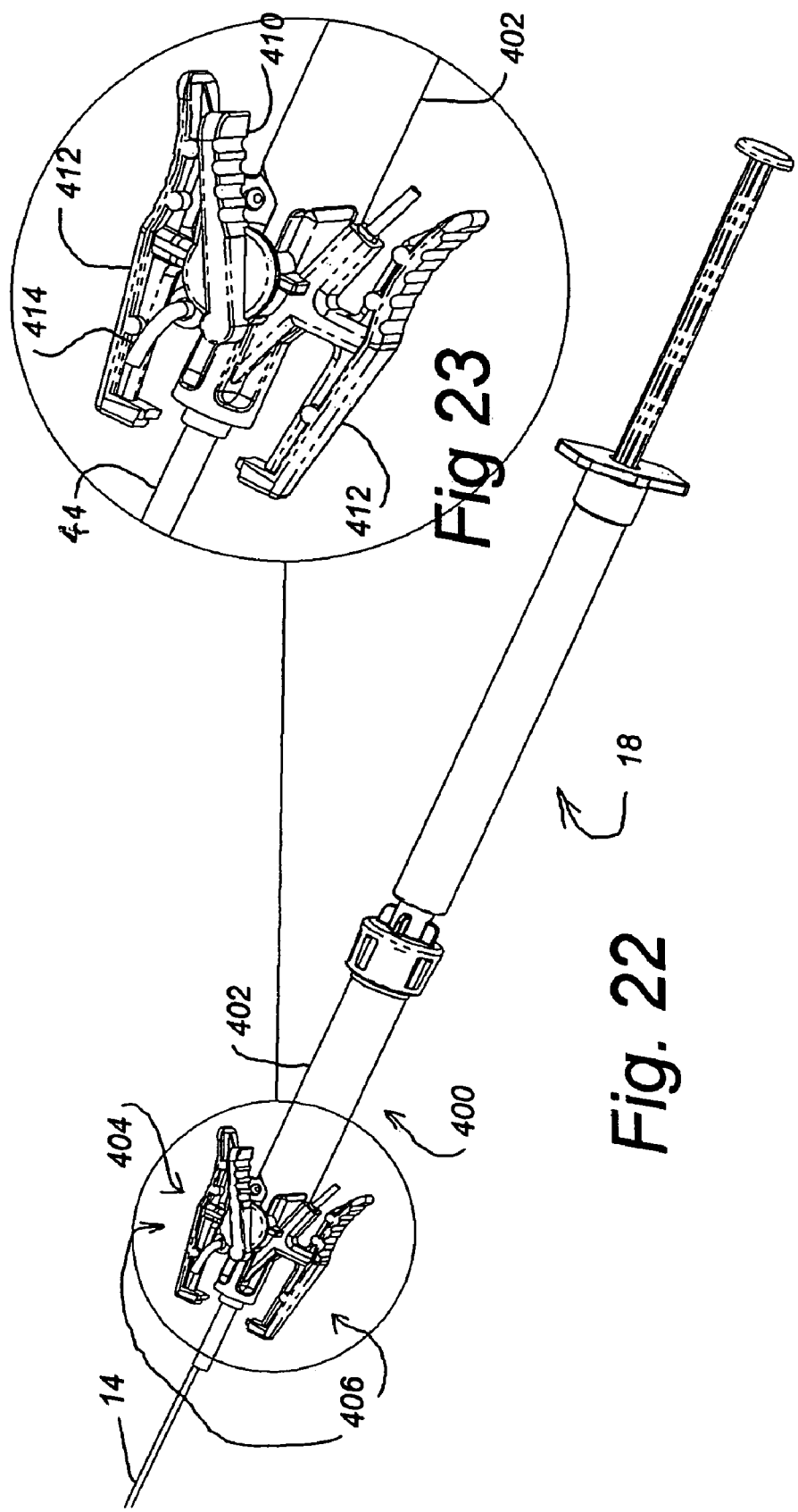

SYSTEM AND METHOD FOR DELIVERING HEMOSTASIS PROMOTING MATERIAL TO A BLOOD VESSEL PUNCTURE WITH A STAGING TUBE

RELATED APPLICATIONS

This application is a continuation in part of prior co-pending U.S. patent application Ser. No. 10/007,204 filed Nov. 8, 2001 and titled SYSTEM AND METHOD FOR DELIVERING HEMOSTASIS PROMOTING MATERIAL TO A BLOOD VESSEL PUNCTURE SITE BY FLUID PRESSURE and a continuation in part of prior co-pending U.S. patent application Ser. No. 10/256,493 filed Sep. 26, 2002 and titled SYSTEM AND METHOD FOR DELIVERING HEMOSTASIS PROMOTING MATERIAL TO A BLOOD VESSEL PUNCTURE SITE BY FLUID PRESSURE.

FIELD OF THE INVENTION

The invention relates to a system and method for delivering hemostasis promoting material to a blood vessel puncture site by fluid pressure, and more particularly, the invention relates to an improved system and method for delivery of absorbable sponge material for sealing of a blood vessel puncture site.

DESCRIPTION OF THE RELATED ART

A large number of diagnostic and interventional procedures involve the percutaneous introduction of instrumentation into a vein or artery. For example, coronary angioplasty, angiography, atherectomy, stenting of arteries, and many other procedures often involve accessing the vasculature through a catheter placed in the femoral artery or other blood vessel. Once the procedure is completed and the catheter or other instrumentation is removed, bleeding from the punctured artery must be controlled.

Traditionally, external pressure is applied to the skin entry site to stem bleeding from a puncture wound in a blood vessel. Pressure is continued until hemostasis has occurred at the puncture site. In some instances, pressure must be applied for up to an hour or more during which time the patient is uncomfortably immobilized. In addition, a risk of hematoma exists since bleeding from the vessel may continue beneath the skin until sufficient clotting effects hemostasis. Further, external pressure to close the vascular puncture site works best when the vessel is close to the skin surface and may be unsuitable for patients with substantial amounts of subcutaneous adipose tissue since the skin surface may be a considerable distance from the vascular puncture site.

More recently, devices have been proposed to promote hemostasis directly at a site of a vascular puncture. One class of such puncture sealing devices features an intraluminal anchor which is placed within the blood vessel and seals against an inside surface of the vessel puncture. The intraluminal plug may be used in combination with a sealing material positioned on the outside of the blood vessel, such as collagen. Sealing devices of this type are disclosed in U.S. Pat. Nos. 4,852,568; 4,890,612; 5,021,059; and 5,061,274.

Another approach to subcutaneous blood vessel puncture closure involves the delivery of non-absorbable tissue adhesives, such cyanoacrylate, to the perforation site. Such a system is disclosed in U.S. Pat. No. 5,383,899.

The application of an absorbable material such as collagen or a non-absorbable tissue adhesive at the puncture site has several drawbacks including: 1) possible injection of the material into the blood vessel causing thrombosis; 2) a lack of pressure directly on the blood vessel puncture which may allow blood to escape beneath the material plug into the surrounding tissue; and 3) the inability to accurately place the absorbable material plug directly over the puncture site.

The use of an anchor and plug system addresses these problems to some extent but provides other problems including: 1) complex and difficult application; 2) partial occlusion of the blood vessel by the anchor when placed properly; and 3) complete blockage of the blood vessel or a branch of the blood vessel by the anchor if placed improperly. Another problem with the anchor and plug system involves reaccess. Reaccess of a particular blood vessel site sealed with an anchor and plug system is not possible until the anchor has been completely absorbed because the anchor could be dislodged into the blood stream by an attempt to reaccess.

A system which addresses many of these problems is described in U.S. Pat. No. 6,162,192 which delivers a hydrated pledget of absorbable sponge material to a location outside the blood vessel to facilitate hemostasis. However, this system involves the removal of the introducer sheath used during the intravascular procedure and the insertion of a dilator and introducer into the tissue tract vacated by the introducer sheath to place the absorbable sponge. It would be desirable to reduce the number of steps involved in delivery of a hemostasis promoting material by allowing the material to be delivered through an introducer sheath already in place within the tissue tract and used in the intravascular procedure.

Accordingly, it would be desirable to provide a system for accurately locating the blood vessel wall at a puncture site and for properly placing a hemostasis plug over the puncture site where the locating and placing steps are performed through the introducer sheath already in place in the blood vessel.

SUMMARY OF THE INVENTION

The present invention relates to a system for delivering hemostasis promoting material to a blood vessel puncture site through a sheath already in place in the blood vessel.

In accordance with one aspect of the present invention, a system for delivering hemostasis promoting material to a blood vessel puncture to facilitate hemostasis includes an introducer sheath having a proximal end and a distal end configured to be inserted into a blood vessel puncture, a hydration chamber configured to receive and hydrate a pledget of hemostasis promoting material, the hydration chamber having a distal end configured to be connected to the proximal end of the introducer sheath and a proximal end configured to be connected to a syringe, and a control tip including a tube having a first diameter and an enlarged distal tip having a second diameter larger than the first diameter.

The tube is configured to extend from an interior of the hydration chamber through the distal end of the hydration chamber, through the introducer, and out the distal end of the introducer.

In accordance with an additional aspect of the present invention, a system for delivering sponge material to a blood vessel puncture to facilitate hemostasis includes an introducer sheath having a proximal end and a distal end configured to be inserted into a blood vessel puncture, a hydration chamber configured to received and hydrate a pledget of sponge material, the hydration chamber having a proximal end and a distal end configured to be connected to the proximal end of the introducer sheath, a syringe connectable to the proximal end of the hydration chamber for delivering the sponge material through the sheath by fluid pressure, and means for preventing the injected sponge material from entering an interior of the blood vessel.

In accordance with a further aspect of the invention, a system for determining a location of a blood vessel puncture for delivery of a hemostasis promoting material to the blood vessel puncture to facilitate hemostasis includes an introducer sheath having a lumen, a proximal end, and a distal end configured to be inserted into a blood vessel puncture, a hemostasis promoting material delivery system having a connector for forming a fluid tight connection with the proximal end of the introducer sheath, and a bleed back exhaust tube having a first end in fluid communication with the lumen of the introducer sheath and a second end positioned to deliver blood to an exterior of the system to provide a visual indication of the location of the distal end of the introducer sheath, wherein the bleed back exhaust tube has in inner diameter of less than 2 mm.

In accordance with another aspect of the invention, a method of promoting hemostasis of a blood vessel puncture includes the steps of injecting a sponge material through an introducer sheath by fluid pressure from a proximal end of the introducer sheath located outside of the body to a distal end of the introducer sheath positioned within a tissue tract extending from the skin to a puncture in a blood vessel, and positioning the injected sponge material at a location outside of a lumen of the blood vessel to promote hemostasis of the blood vessel puncture.

In accordance with an additional aspect of the invention, a method of promoting hemostasis of a blood vessel puncture includes the steps of positioning an introducer sheath in a tissue tract extending from the skin of a patent into a blood vessel, performing an intravascular procedure through the introducer sheath positioned in the tissue tract, connecting a hemostasis promoting material delivery system to the introducer sheath without removing the introducer sheath, and delivering the hemostasis promoting material through the introducer to the tissue tract by fluid pressure.

In accordance with a further aspect of the invention, a system for delivering hemostasis promoting material to a blood vessel puncture to facilitate hemostasis includes a hemostasis promoting material delivery system containing a hemostasis promoting material and a connector positioned on a distal end of the hemostasis promoting material delivery system. The connector is configured to form a removable fluid tight seal with an introducer sheath by connecting to a flange of the introducer sheath.

In accordance with another aspect of the invention, a pledget handling system is provided. The pledget handling system facilitates consistent hydration of the pledget, provides for effective staging of the pledget, prevents early pledget delivery, and allows the user to effectively manage the bleed back process.

In accordance with another aspect of the invention, the pledget handling system includes a sheath connector with which the user can easily connect the pledget handling system to an introducer sheath having a variety of designs.

In accordance with another aspect of the invention, the pledget handling system includes a bleed back control system which permits the user to direct the flow of blood away from the user or other personnel.

BRIEF DESCRIPTION OF THE DRAWING FIGURES

The invention will now be described in greater detail with reference to the preferred embodiments illustrated in the accompanying drawings, in which like elements bear like reference numerals, and wherein:

FIG. 3C is a side cross sectional view of a portion of FIG. 2 according to a second alternative embodiment in a first position.

FIG. 3D is a side cross sectional view of FIG. 3C in a second position.

FIG. 22 is a view of the pledget handling system of one embodiment of the present invention.

FIG. 23 is enlarged view of a portion of the embodiment in FIG. 22.

DETAILED DESCRIPTION OF THE PREFERRED EMBODIMENTS

A system for delivering hemostasis promoting material of the present invention allows the hemostasis promoting material to be delivered to a blood vessel puncture site by fluid pressure. The system allows the hemostasis promoting material to be delivered through an introducer sheath which is already in place within a tissue tract. This system includes a control tip which is insertable through the introducer sheath to locate and occlude the blood vessel puncture site and a hydration chamber for receiving and delivering the hemostasis promoting material to the blood vessel puncture site.

Although the present invention is particularly designed for delivering a hemostasis promoting material in the form of an absorbable sponge through the introducer sheath by fluid pressure, it should be understood that the system may also be used for delivering other hemostasis promoting materials which are useful for sealing a puncture site. The use of an absorbable hydrated sponge material allows the delivery of more absorbable sponge material down through a smaller sheath by allowing the sponge material to be hydrated and compressed. Once delivered, the absorbable sponge rapidly expands to fill the entire width of the tissue tract and provides hemostasis at the puncture site.

In the context of the present invention, "pledget" means a piece of sponge formed into a generally elongated shape having a size which allows delivery in a hydrated state through a delivery cannula or introducer to a site of a puncture in a blood vessel.

"Sponge" means a biocompatible material which is capable of being hydrated and is resiliently compressible in a hydrated state. Preferably, the sponge is non-immunogenic and may be absorbable or non-absorbable.

"Absorbable sponge" means sponge which, when implanted within a human or other mammalian body, is absorbed or resorbed by the body.

"Hydrate" means to partially or fully saturate with a fluid, such as saline, water, contrast agent, thrombin, therapeutic agents, or the like.

Figure 1:
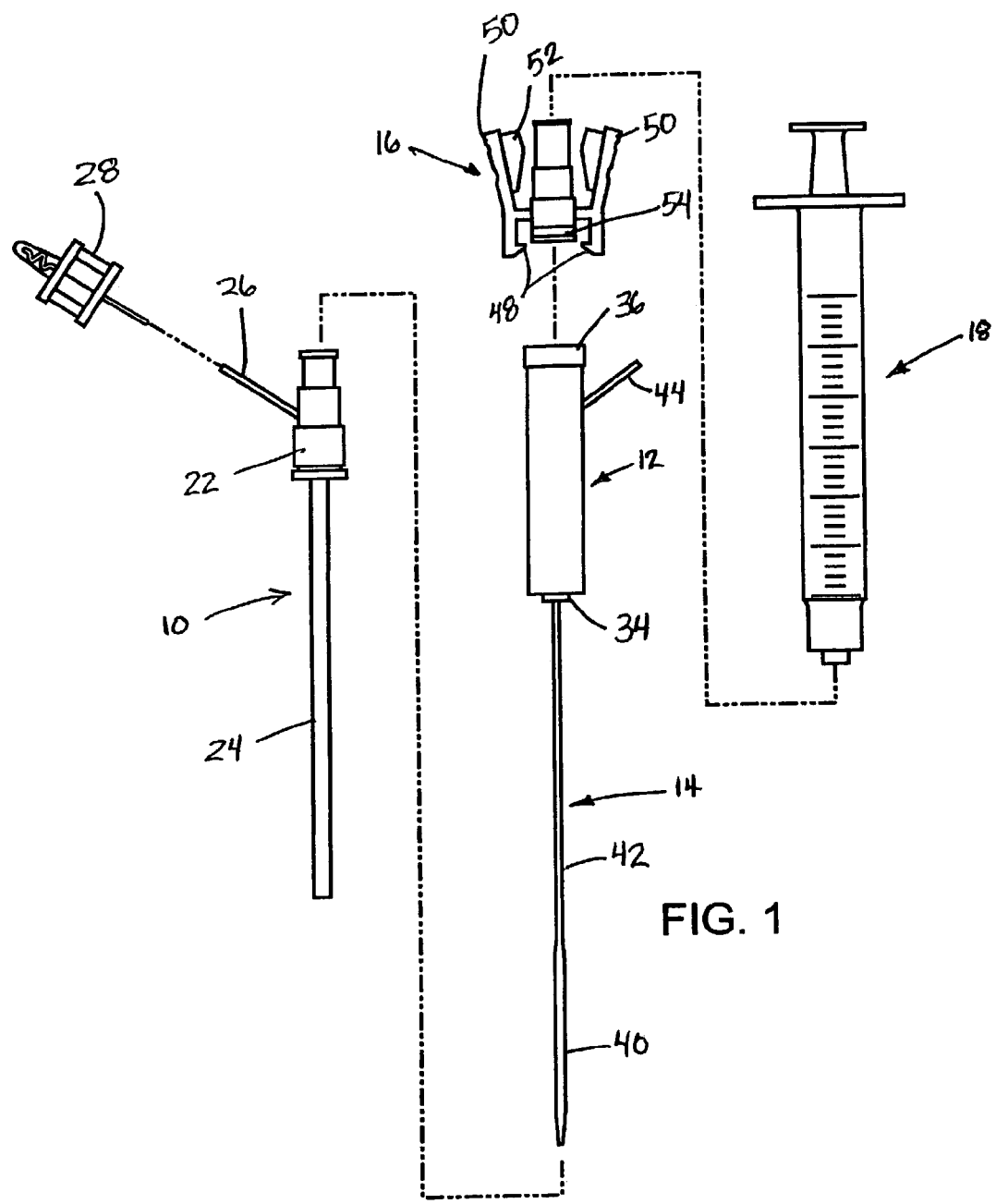
FIG. 1 is an exploded side view of a first embodiment of a system for delivering hemostasis promoting material to a blood vessel puncture site by fluid pressure.

The system of FIG. 1 includes an introducer sheath 10, a hydration chamber 12 with an attached control tip 14, a coupler 16, and a syringe 18. The introducer sheath 10 is an intravascular access sheath as is conventionally used for procedures such as coronary angioplasty and stenting procedures. The introducer sheath 10 includes a proximal hub 22 connected to a tubular sheath 24. A vent tube 26 is in fluid communication with an interior of the hub 22 for purposes of providing a visual bleed back indication which will be discussed in further detail below. In the embodiment illustrated in FIG. 1, a vent cap 28 is provided for opening and closing the vent tube 26 manually. However, other vent opening and closing mechanisms will be described in further detail below with respect to FIGS. 3B–3G.

The hydration chamber 12 is configured to receive a pledget of absorbable sponge material for hydration of the pledget and delivery of the pledget through the introducer sheath 10. A proximal end of the hydration chamber 12 includes a flange 36 or other connecting element for receiving the coupler 16. A distal end 34 of the hydration chamber 12 connects to the proximal hub 22 of the introducer sheath 12. The control tip 14 has an enlarged distal end 40 configured to be received in the puncture in the blood vessel and to control blood flow through the puncture in the blood vessel. The enlarged distal end 40 is connected to a smaller diameter control tip tube 42 which extends from the enlarged distal end through the distal end of the hydration chamber 12 and out a side of the hydration chamber 12 to a proximal end 44 of the control tip. The enlarged distal end 40 of the control tip performs the multiple functions of controlling blood flow through the blood vessel puncture, providing an indication of the position of the distal end of the introducer sheath, and guiding the hemostasis promoting material delivery system over a guidewire.

The coupler 16 allows the syringe 18 to be connected to the hydration chamber 12. Removal of the coupler 16 from the hydration chamber 12 allows the pledget of absorbable sponge material to be easily inserted into the hydration chamber in its dry form. Upon connection of the coupler 16 to the hydration chamber 12 the conventional syringe 18 will be connected to the coupler 16 for injection of fluid into the hydration chamber. The coupler 16 includes a seal 54 and two or more locking tabs 48 which lock over the flange 36 of the hydration chamber and are releasable by pressing on two wings 50 of the coupler. Stops 52 on the interior surfaces of the wings 50 prevent the coupler 16 from being removed from the hydration chamber 12 when a syringe 18 is mounted on the coupler. It should be understood that many other coupler designs may also be used without departing from the present invention.

Figure 2:
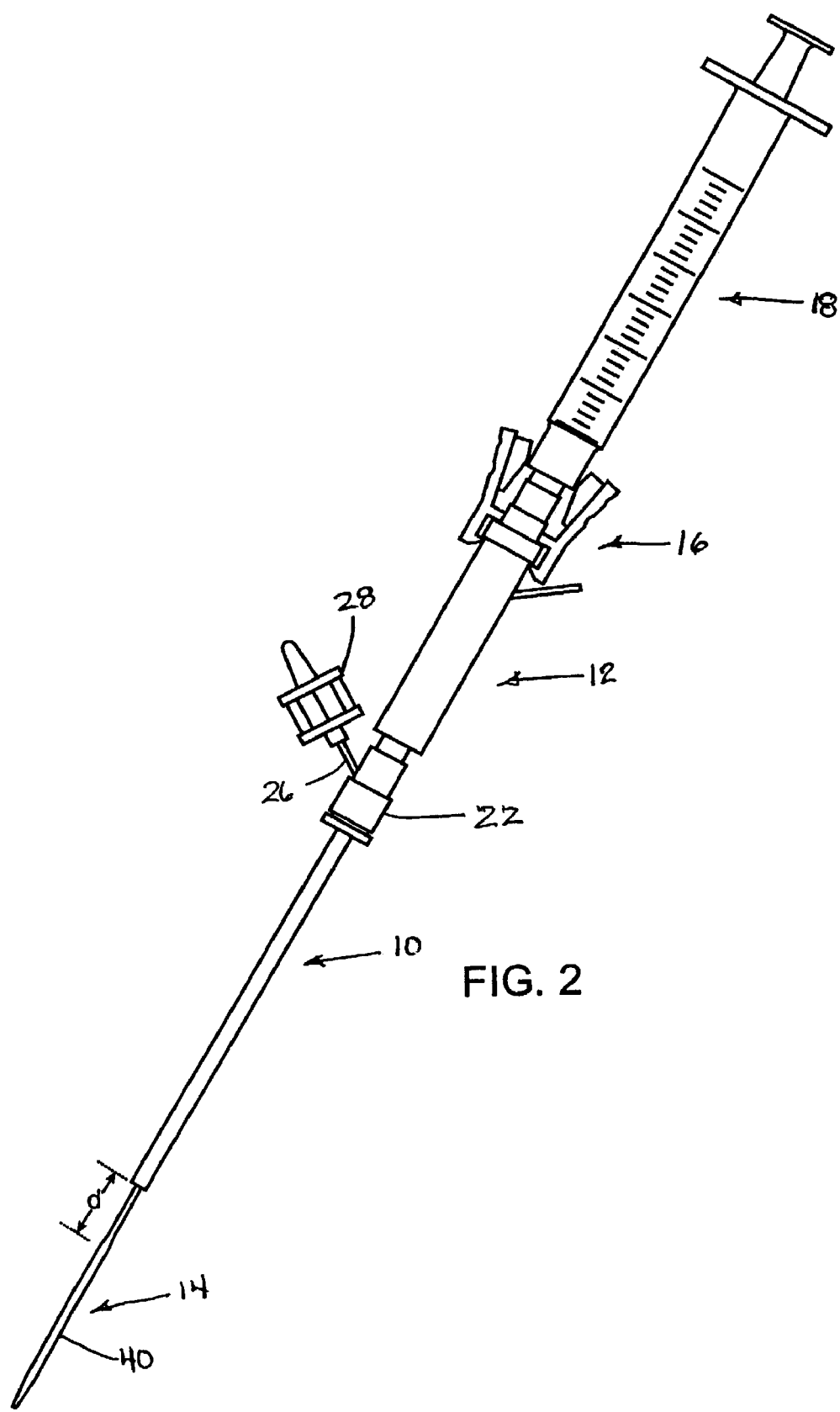
FIG. 2 is an assembled side view of the system of FIG. 1.
Figure 3A:
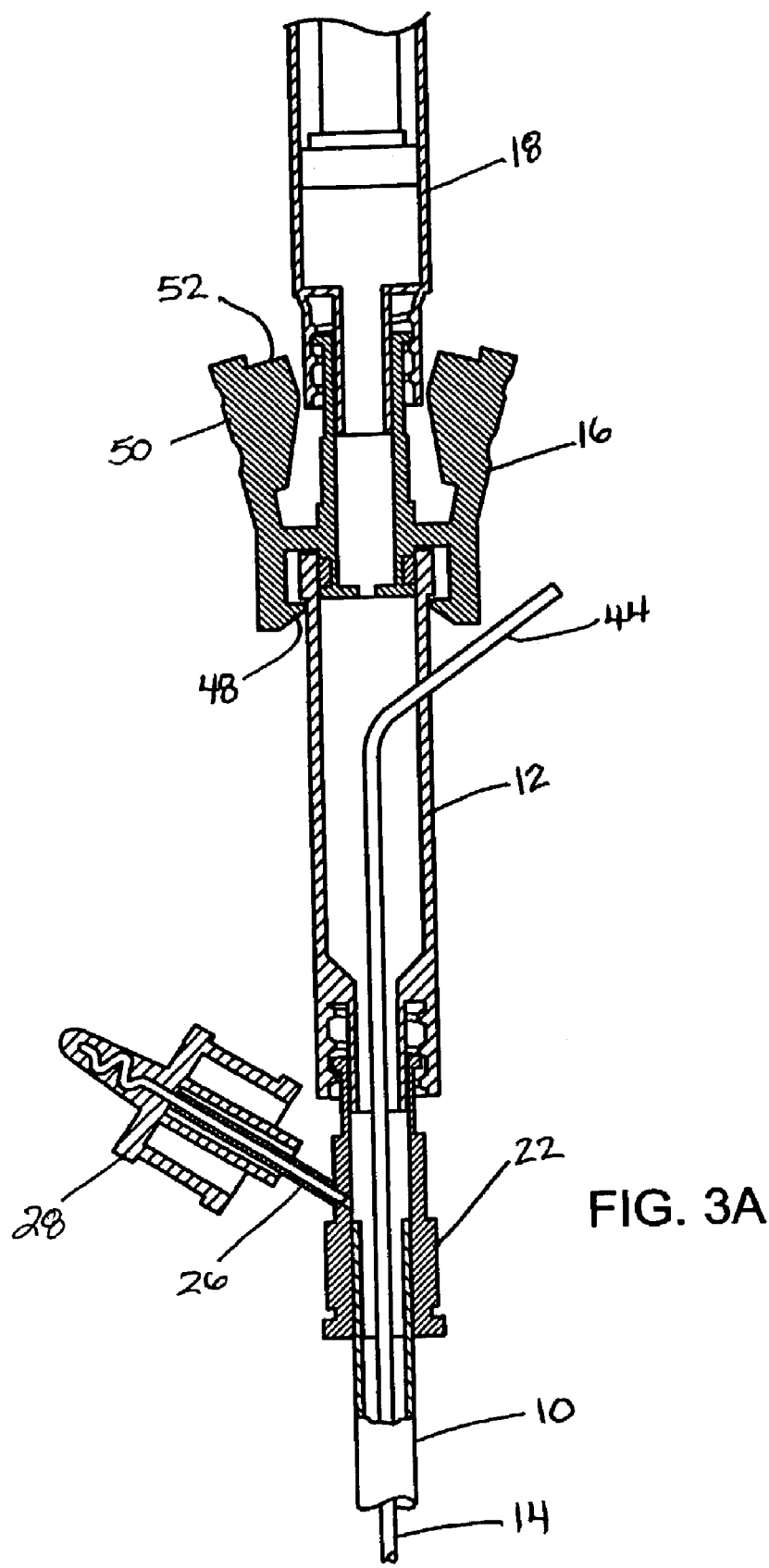
FIG. 3A is a side cross sectional view of a portion of the system of FIG. 2.

In use, the system of FIGS. 1, 2, and 3A is assembled with a sponge placed inside the hydration chamber 12 and a syringe 18 containing water, saline solution, or other fluid attached to the hydration chamber by the coupler 16. The sponge is hydrated and staged or moved, to a position at the distal end of the hydration chamber as will be described in further detail below. The syringe 18 is preferable capable of generating a high pressure with a relatively low plunger force such as a 1 cc syringe.

The introducer sheath 10 is placed in the blood vessel puncture of a patient in a conventional manner for performance of the intravascular procedure. After the intravascular procedure, the introducer sheath 10 and a guidewire (not shown) are maintained in place extending into the blood vessel. The control tip 14 is threaded over the proximal end of the guidewire and the hydration chamber 12 and control tip 14 are advanced into the introducer sheath until the hydration chamber distal end 34 is engaged with the hub 22 of the introducer sheath 10. Bleed back is observed by a variety of methods which will be described below with respect to FIGS. 3A–3G. In the embodiment of FIG. 3A, the vent cap 28 is removed from the vent tube 26 to observe bleed back. The introducer sheath 10, hydration chamber 12, and control tip 14, are withdrawn together slowly from the puncture site until the bleed back observed from the vent tube 26 stops. The bleed back stops when the enlarged distal end 40 of the control tip 44 is positioned in the blood vessel puncture preventing blood from escaping from the puncture.

The distance d between the distal end of the tubular sheath 24 and the enlarged distal end 40 of the control tip 14 is selected so that the point at which bleed back stops indicates that the distal end of the introducer sheath 10 is located at a desired delivery location for delivery of the hemostasis promoting material to the blood vessel puncture site. The distance d will be selected to correspond to the size of the pledget to be delivered to the puncture site and will be selected such that the hemostasis promoting material is located in the tissue tract adjacent the blood vessel without extending into the lumen of the blood vessel.

FIG. 3A illustrates a first embodiment of a vent tube 26 with a vent cap 28 for observing bleed back. When the vent cap 28 is removed from the vent tube 26 blood is able to pass from the distal end of the introducer sheath 10 through the introducer sheath and out of the vent tube. The vent tube 26 has a relatively small diameter which is selected to provide a very noticeable spurt or stream of blood to indicate bleed back has occurred. In contrast, the observance of bleed back from a larger tube such as the introducer sheath would result in an oozing or dripping bleed back indication which is difficult for the user to use as a precise indicator of position. According to one preferred embodiment, the vent tube 26 has an inner diameter of about 0.4 mm to about 2 mm, preferably about 1 mm.

Figure 3B:
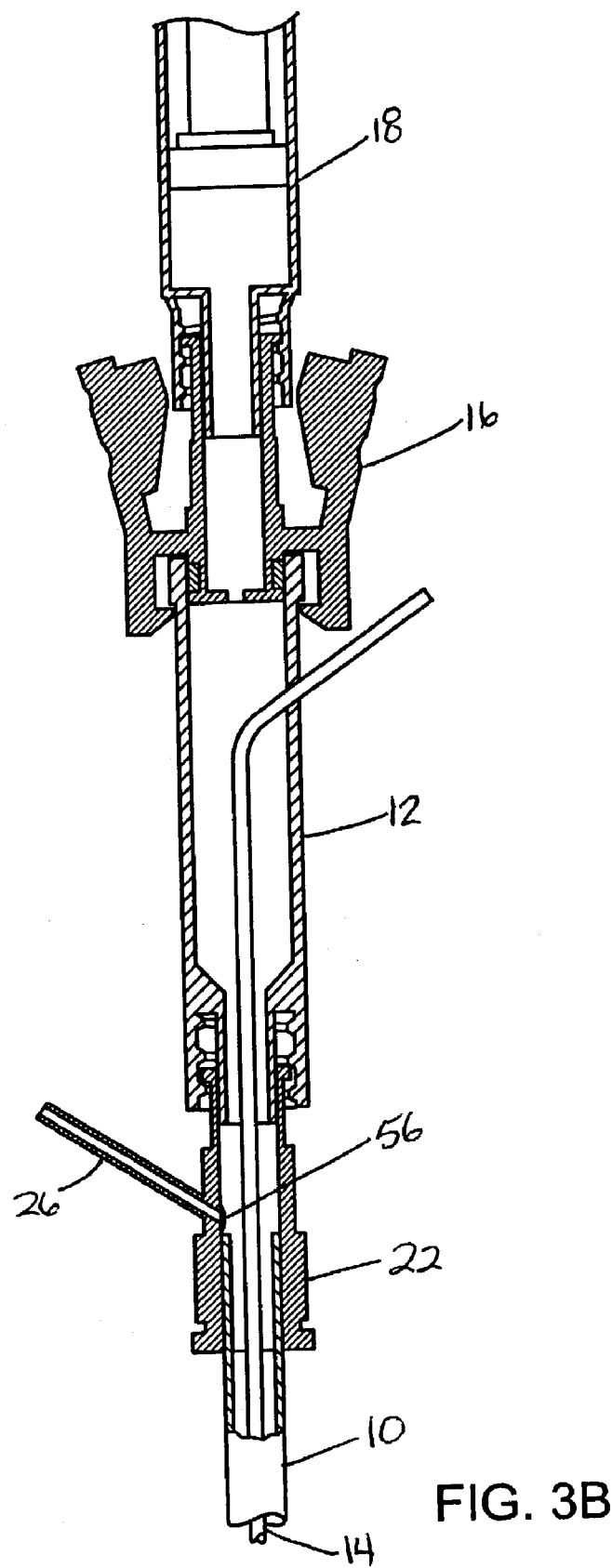
FIG. 3B is a side cross sectional view of a portion of FIG. 2 according to a first alternative embodiment with a flapper valve.

FIG. 3B illustrates an alternative to manually placing the vent cap 28 into the vent tube 26 after bleed back has been used to locate the desired position for delivery of the hemostasis promoting material. In FIG. 3B, a flapper valve 56 is positioned over an inlet of the vent tube 26 inside the introducer hub 22. The flapper valve 56 responds to the sudden extreme pressures of delivering of the hemostasis promoting material and closes over the inlet to the vent tube 26. Any of the known types of flapper valves may be used in the embodiment of FIG. 3B.

FIG. 3C illustrates a further alternative embodiment for opening and closing the vent tube 26. FIG. 3C illustrates a hydration chamber 12A with an extended cylindrical distal end 60. In the position illustrated in FIG. 3C, the inlet to the vent tube 26 is opened. Upon advancement of the hydration chamber 12A with respect to the introducer sheath 10 by rotation of the hydration chamber the distal end 60 of the hydration chamber covers the inlet to the vent tube 26, as shown in FIG. 3D.

Figure 3E:
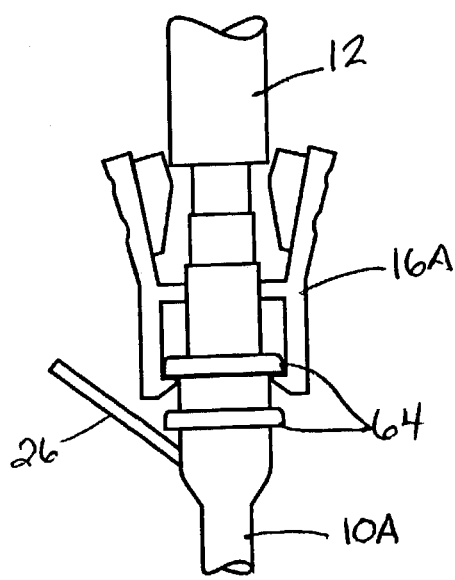
FIG. 3E is a side view of a portion of the system of FIG. 2 according to a third alternative embodiment with a two position connecting system.
Figure 3F:
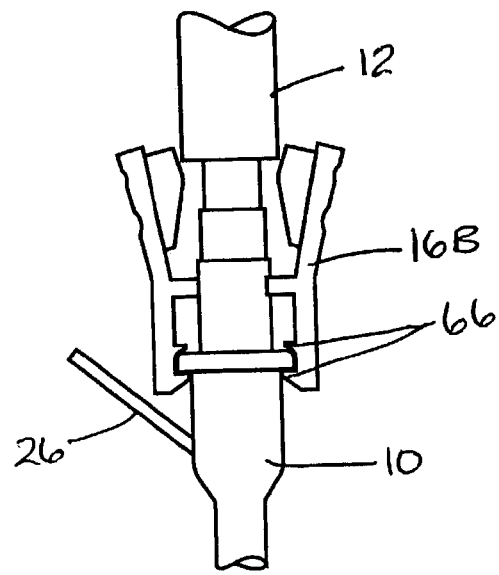
FIG. 3F is a side view of a portion of the system of FIG. 2 according to a fourth embodiment with an alternative two position connecting system.
Figure 3G:
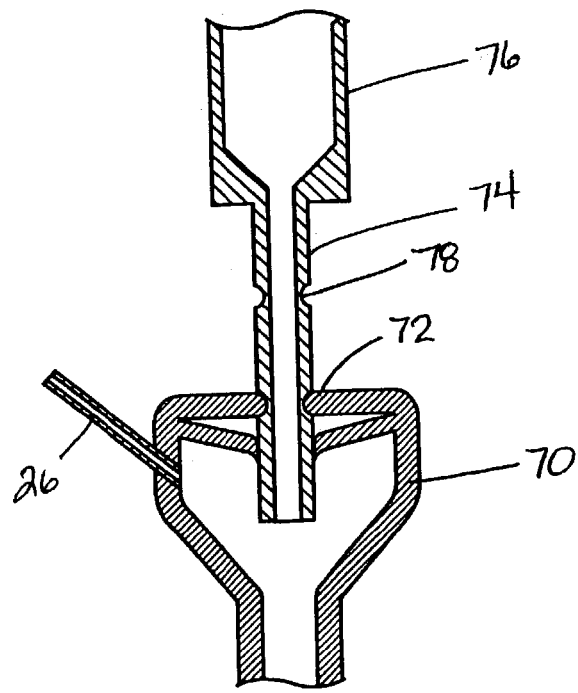
FIG. 3G is a side cross sectional view of a portion of the system of FIG. 2 according to a fifth embodiment with another alternative two position connecting system.

FIGS. 3E, 3F, and 3G illustrate three further embodiments of a two position hydration chamber which may be advanced after bleed back is observed to cover the inlet to the vent tube 26 and prevent exhaust through the vent tube during delivery of the hemostasis promoting material. FIG. 3E illustrates a modified coupler 16A which can be connected to the hydration chamber 12 and is advanced to two different positions by locking on two sequential annular rings 64 provided on a introducer sheath 10A.

In the embodiment illustrated in FIG. 3F the two positions of the hydration chamber 12 with respect to the introducer sheath 10 are provided by a coupler 16B having two sets of locking tabs 66 for locking the coupler 16 in two locations on the introducer sheath 10.

FIG. 3G illustrates an alternative embodiment of a sheath hub 70 having an inner locking annulus or flange 72 at a proximal end. A distal end 74 of a hydration chamber 76 is provided with two locking grooves 78 which snap into the locking annulus 72. In the first position shown in FIG. 3G, the vent tube 26 is opened. When the hydration chamber 76 is advanced further into the introducer sheath 70 the distal end 74 of the hydration chamber passes the vent tube 26 and prevents pressure loss.

Figure 4:
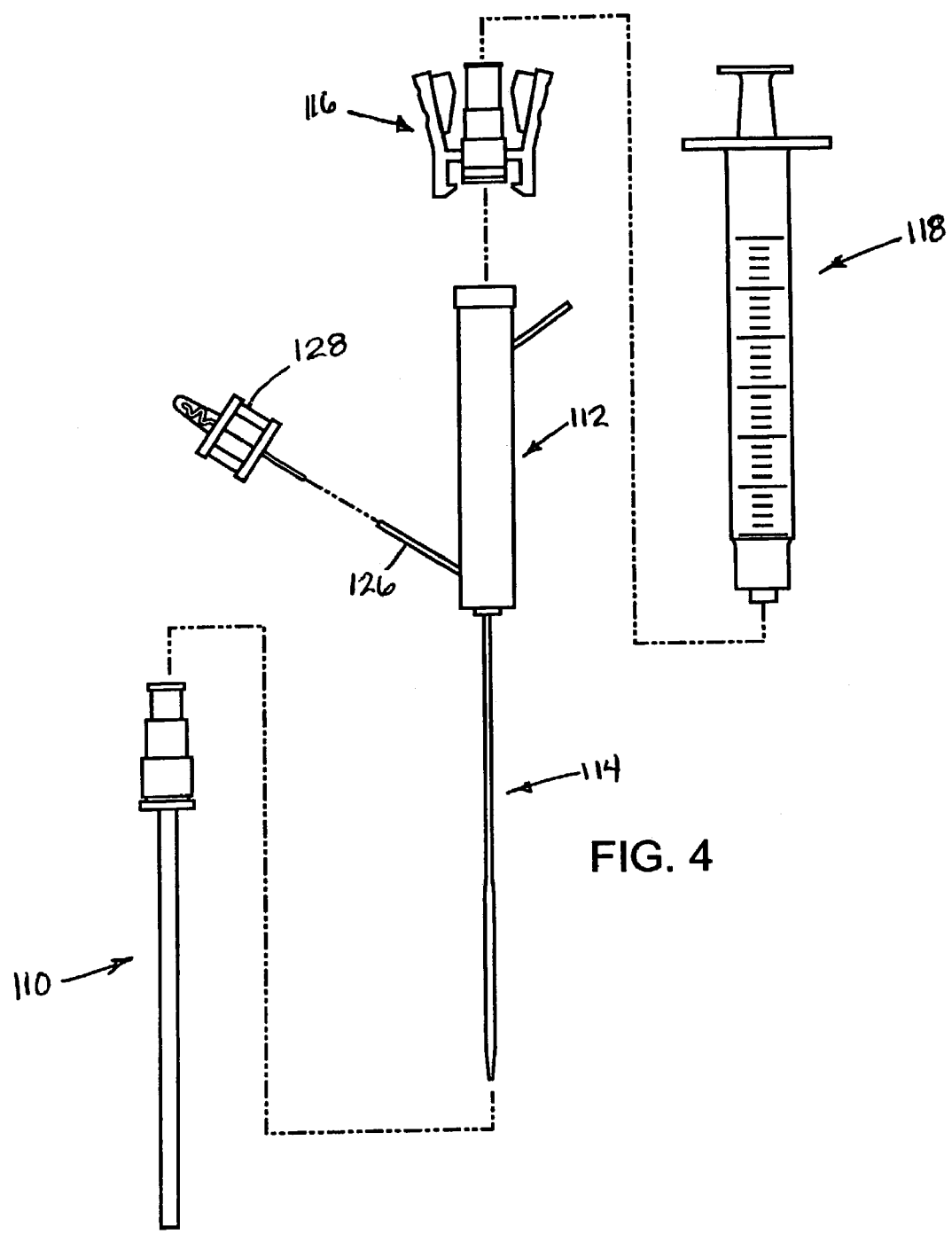
FIG. 4 is an exploded side view of an alternative system for delivering hemostasis promoting material to a blood vessel puncture site by fluid pressure.
Figure 5:
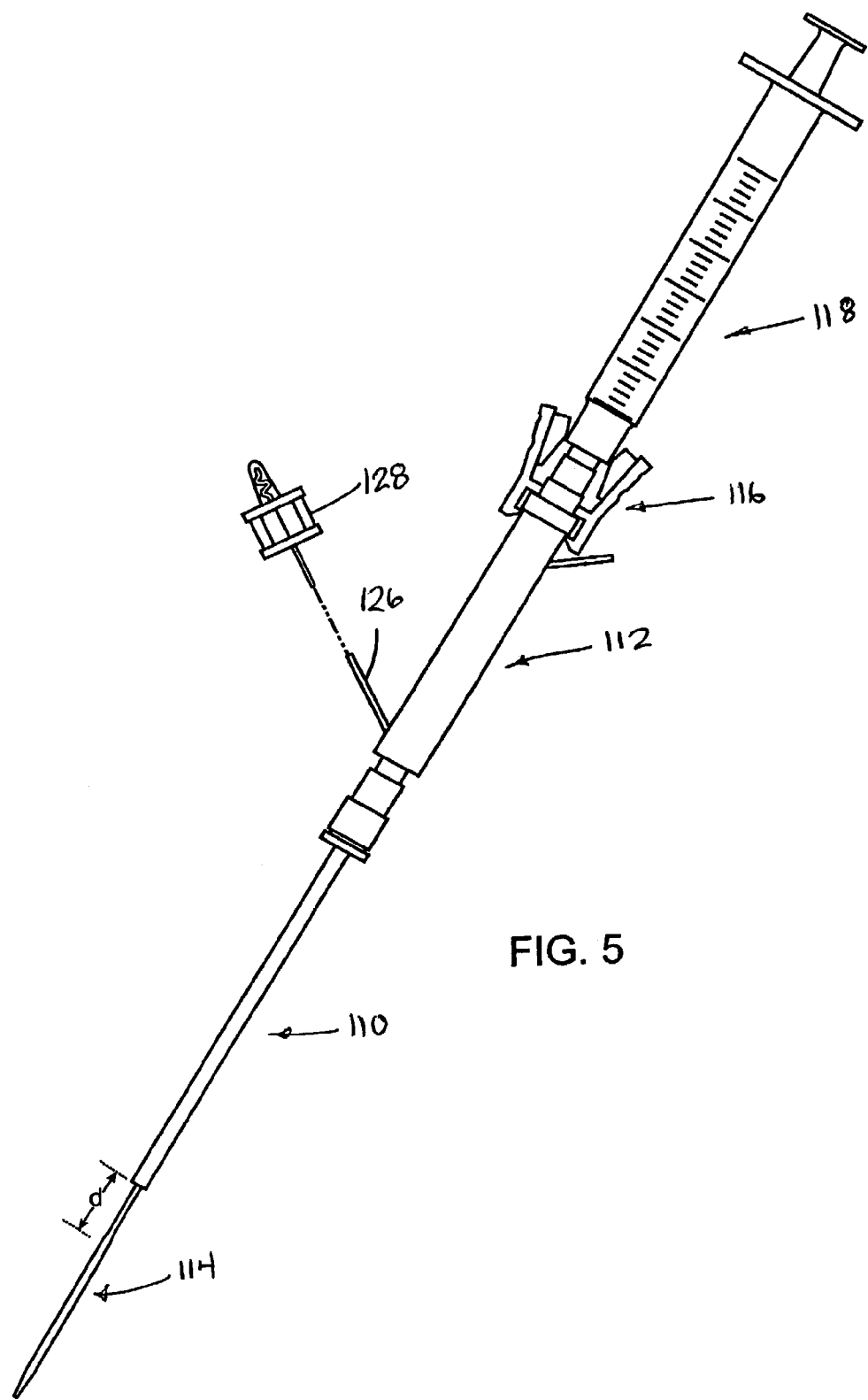
FIG. 5 is an assembled side view of the system of FIG. 4.
Figure 6:
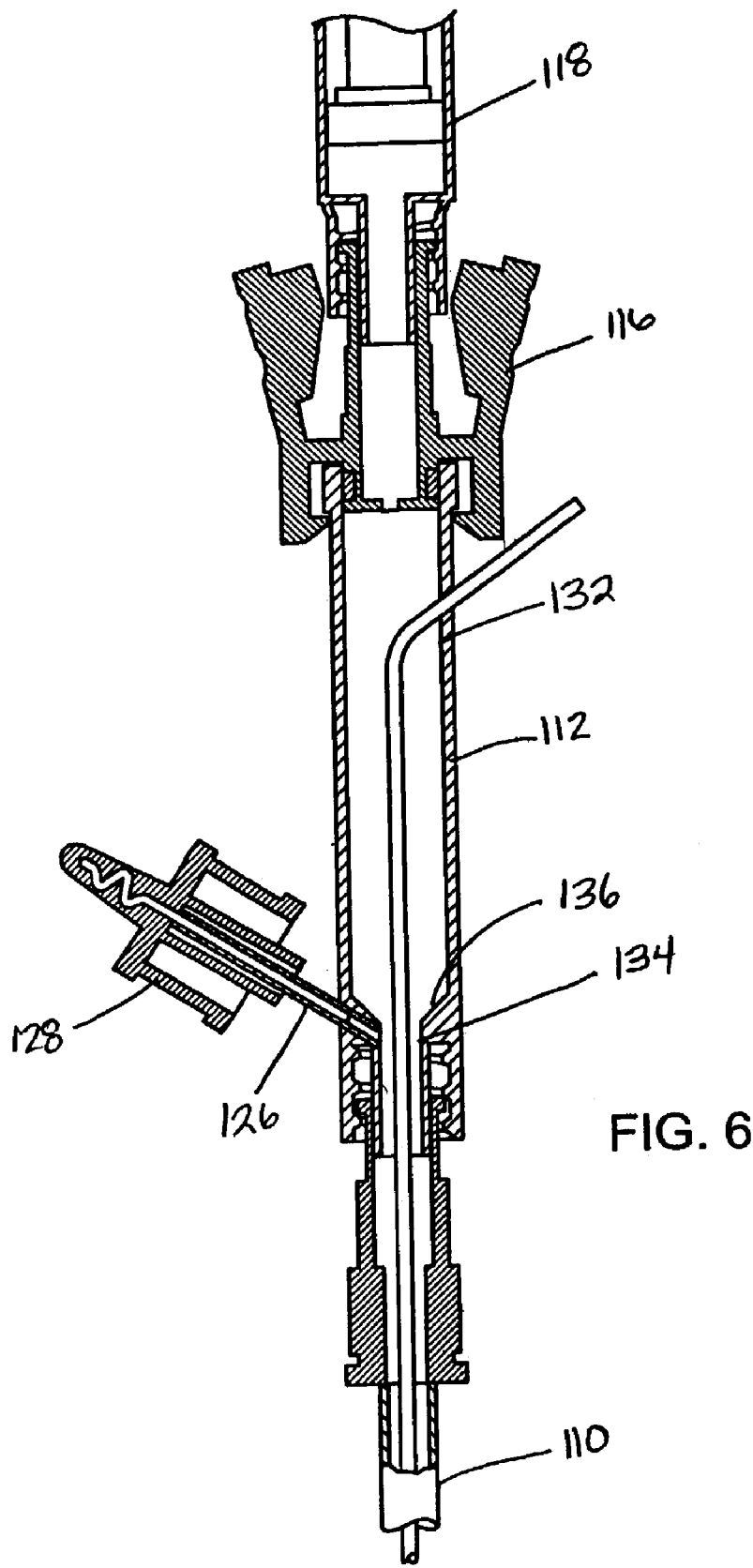
FIG. 6 is a side cross sectional view of a portion of the system of FIG. 5.

FIGS. 4–6 illustrate an alternative embodiment of a system for delivering hemostasis promoting material to a blood vessel puncture site including another option for observing bleed back. FIG. 4 illustrates an introducer sheath 110, a hydration chamber 112, a control tip 114, a coupler 116, and a syringe 118. According to this embodiment, a vent tube 126 extends from a side of a distal end of the hydration chamber 112. The vent tube 126 may be provided with a vent cap 128 for manually opening and closing the vent tube 126. Alternatively, the vent tube closure system illustrated in FIG. 3B may be used. In the embodiment illustrated in FIGS. 4–6, the introducer sheath 110 may be any of those introducer sheaths which are currently used and may be connectable to the hydration chamber 112 by a lure lock connection as shown or by a coupler 16 or other coupling mechanisms as necessary. As shown most clearly in the cross sectional view of FIG. 6, the hydration chamber 112 includes a large inner diameter at a proximal end 132 and a small inner diameter distal end 134. The vent tube 126 is provided along the smaller inner diameter distal end 134 of the hydration chamber 112 distally of a tapered portion 136 of the hydration chamber. In this embodiment, the hydrated sponge should have a distal end which is positioned just proximally of the vent tube inlet so that the sponge does not block the inlet of the vent tube restricting the bleed back pathway. The system of FIGS. 4–6, provides the advantage that the hydration chamber 112 and control tip 114 may be used with any of the known introducer sheaths 110 which may be in use in any particular intravascular procedure.

Figure 7:
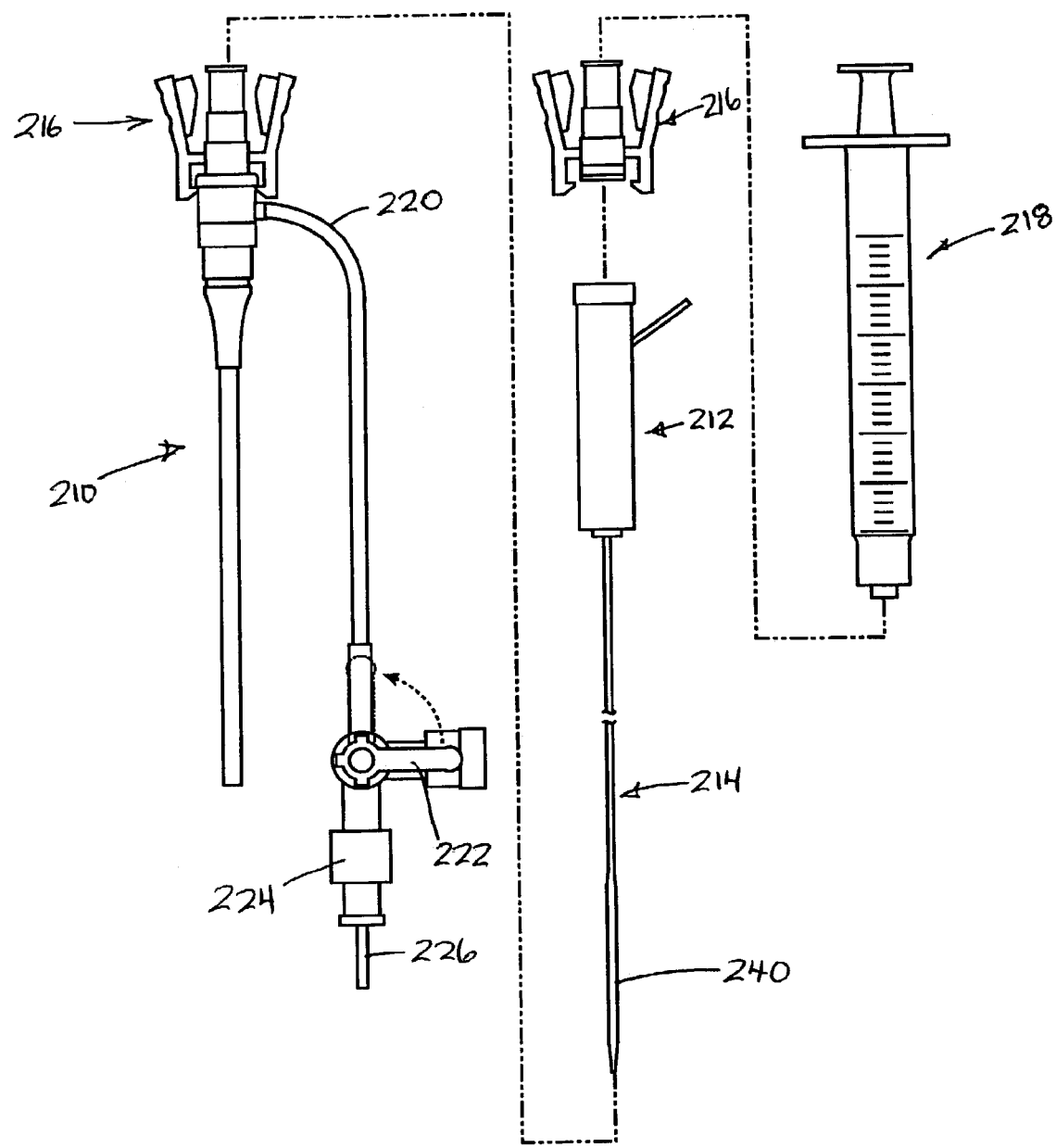
FIG. 7 is an exploded side view of another embodiment of a system for delivering hemostasis promoting material to a blood vessel puncture site by fluid pressure.
Figure 8:
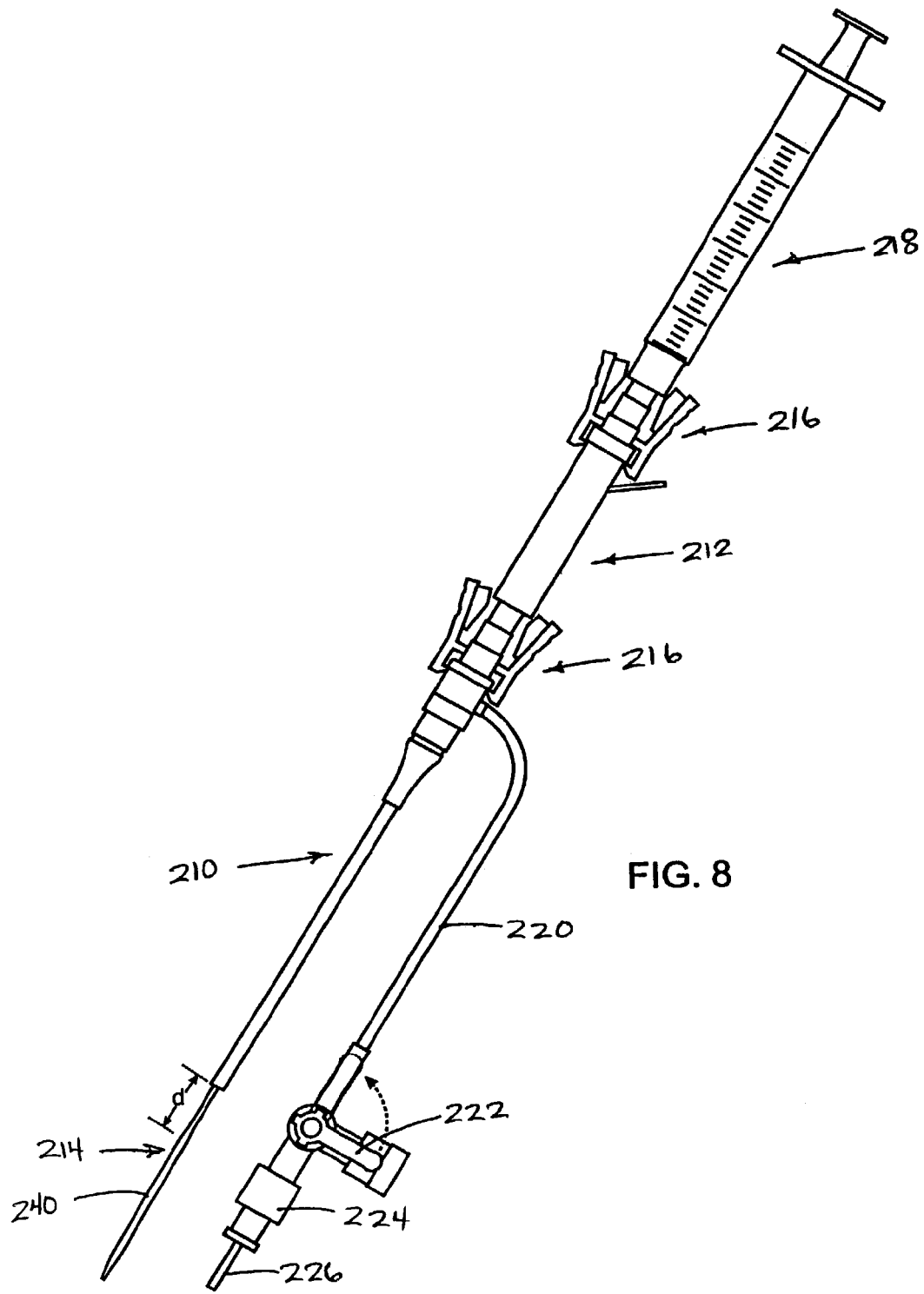
FIG. 8 is an assembled side view of the system of FIG. 7.
Figure 9:
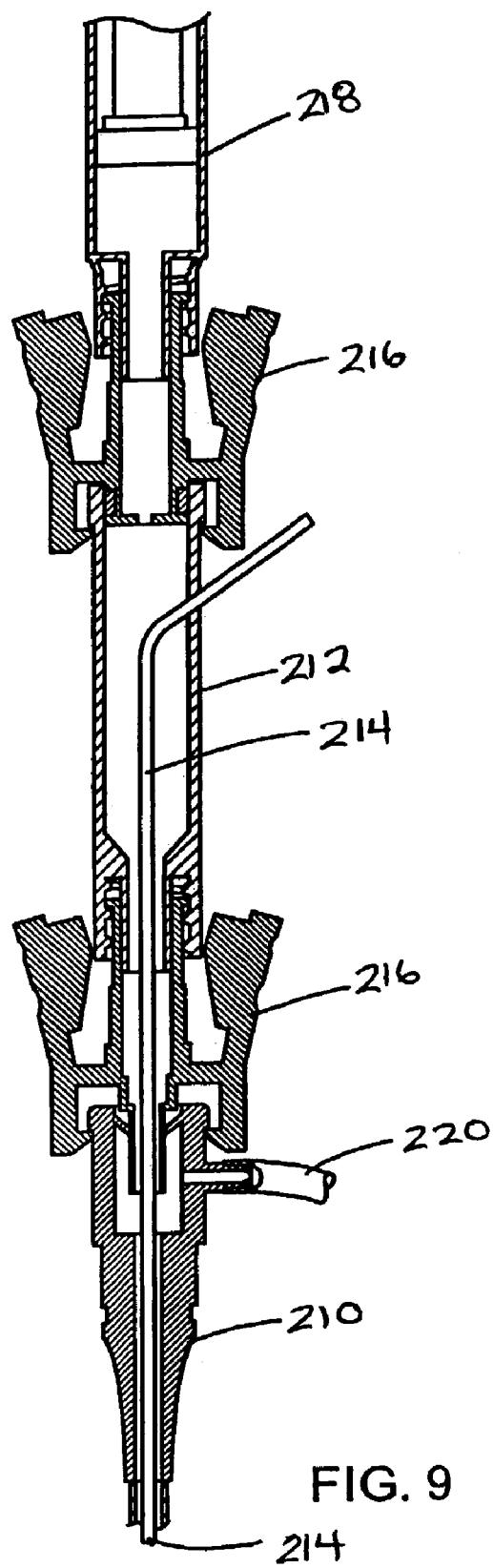
FIG. 9 is a side cross sectional view of a portion of the assembled system of FIG. 7.
Figure 10:
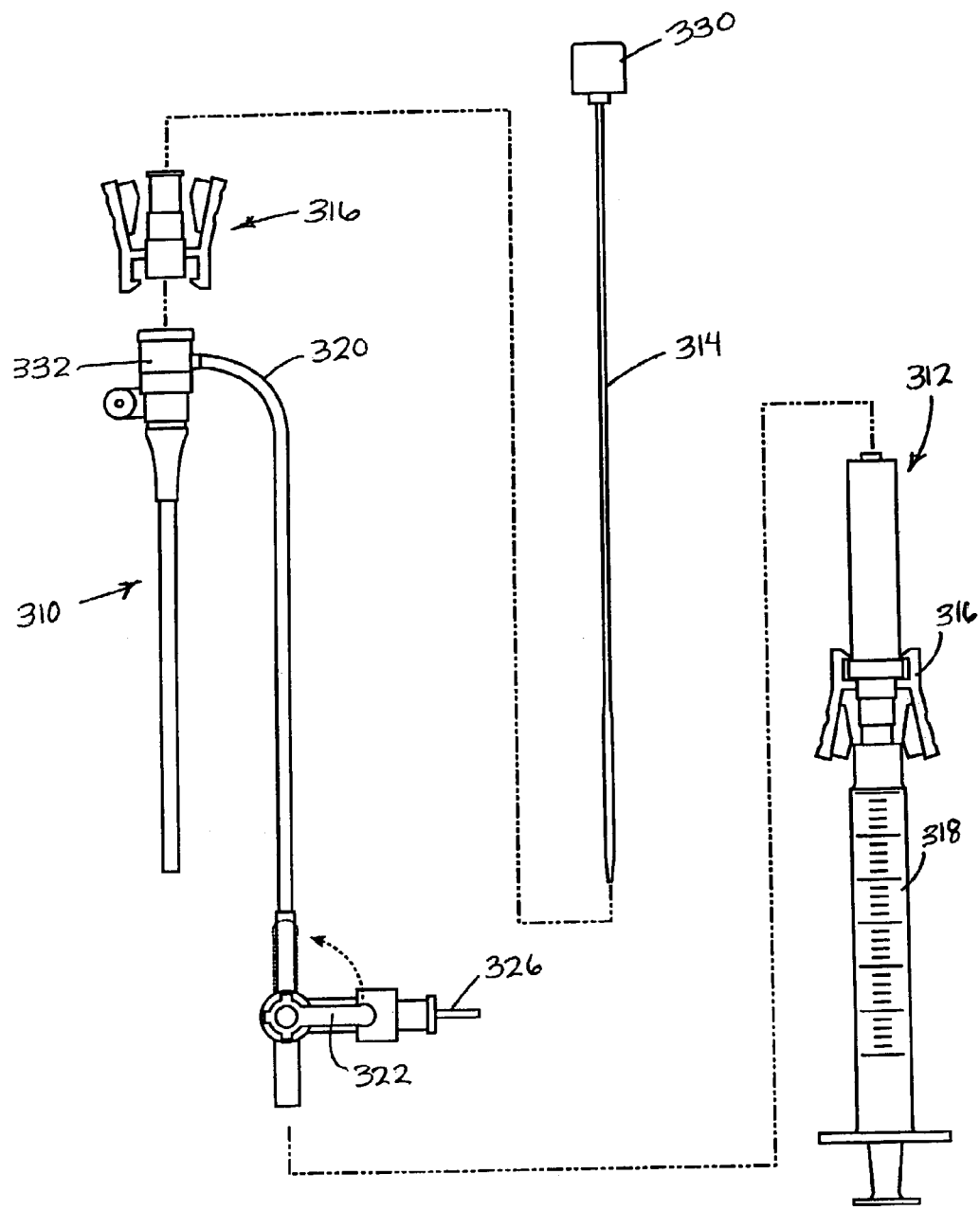
FIG. 10 is an exploded side view of a further system for delivering hemostasis promoting material to a blood vessel puncture site by fluid pressure with the material delivered to a side branch of the sheath.
Figure 11:
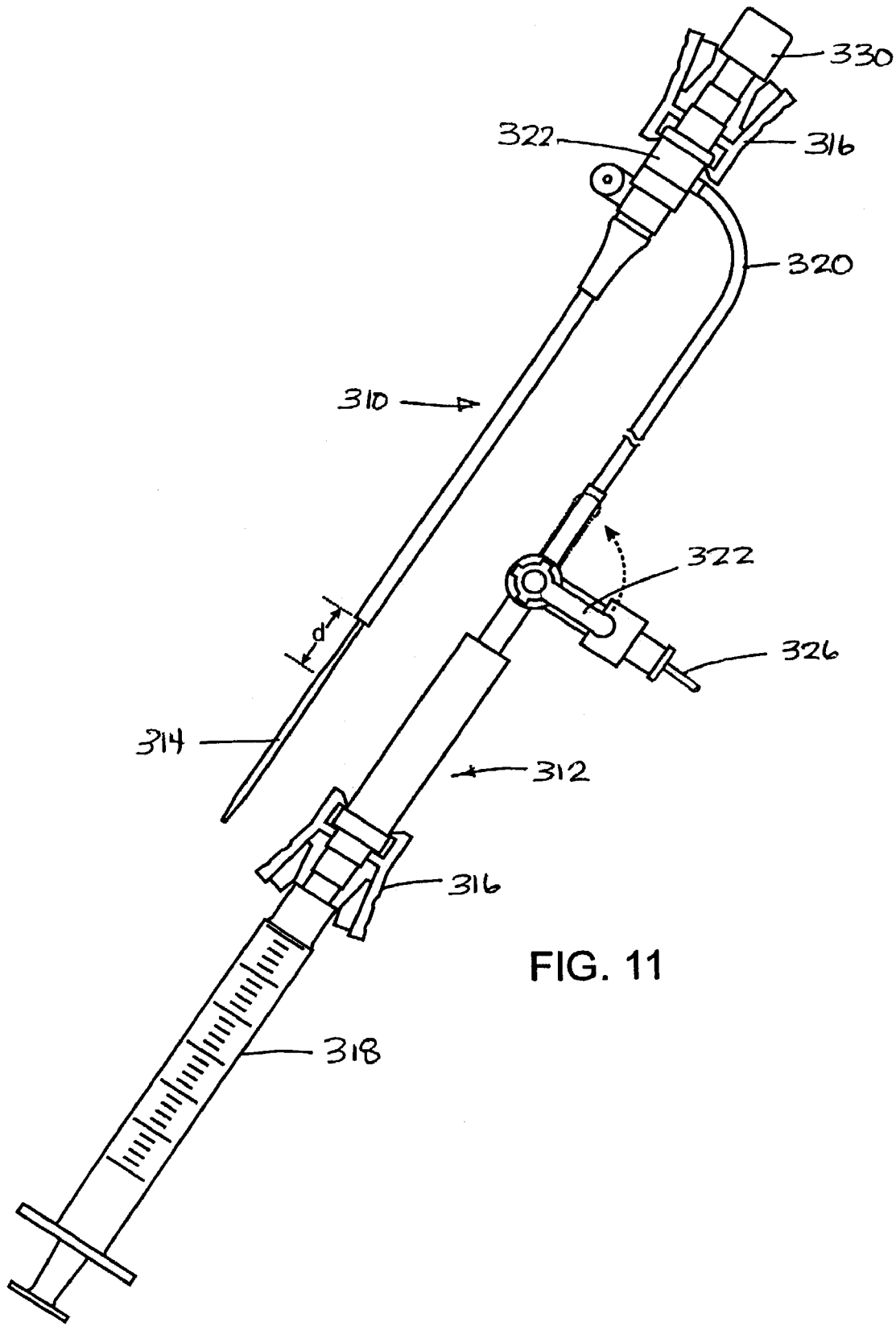
FIG. 11 is an assembled side view of the system of FIG. 10.

FIGS. 7–9 illustrate an alternative system for delivering hemostasis promoting material using a known introducer sheath 210 with an attached side port. FIG. 7 illustrates the introducer sheath 210, the hydration chamber 212 with the attached control tip 214, a coupler 216, and a syringe 218. The hydration chamber 212 may be connected to the introducer sheath 210 by a lure lock connection as described above or by an additional coupler 216 in the event that the introducer sheath 210 is not provided with a proximal lure connector.

The introducer sheath 210 of FIG. 7 includes a side port 220 which is used to view bleed back from the blood vessel puncture site. Connected to the side port 220 is a conventional stop cock valve 222 which is moveable between the open position illustrated in FIG. 7 and a closed position illustrated in phantom in FIG. 7.

As discussed above, preferably the bleed back is viewed when exiting a vent having a relatively small diameter. Accordingly, a small diameter vent tube 226 is preferable connected to one of the ports 224 of the side port 220. The vent tube 226 has a relatively small diameter and thus provides the desired blood spurt as a bleed back indicator. The vent tube 226 may be connected to one of the ports 224 by any of the known connectors or may be provided integrally with the port. In use, of the embodiment of FIGS. 7–9, the stop cock 122 is opened to observe bleed back passing through the introducer sheath and out the vent tube 226. The introducer sheath 210 and hydration chamber 212 are then withdrawn slowly until the bleed back is stopped by the presence of the enlarged distal end 240 of the control tip 214 in the blood vessel puncture. Once bleed back has stopped the stop cock 222 is closed to prevent fluid pressure loss from the introducer sheath 210 while the syringe plunger is depressed to advance the sponge through the introducer sheath 210 to the desired delivery location at the blood vessel puncture site.

FIGS. 10–13 illustrate a further alternative embodiment of a system for delivering hemostasis promoting material in which a hydration chamber 312 is connected to a side port 320 of an introducer sheath 310. The vent tube 326 is connected to another port of the side port 320. The stop cock 322 is movable between an open delivery position shown in FIG. 10 and a closed bleed back position shown in phantom in FIG. 10. In the closed bleed back position, bleed back is allowed through the vent tube 326. In the open delivery position the hemostasis promoting material is delivered from the hydration chamber 312 to the introducer sheath.

Figure 13:
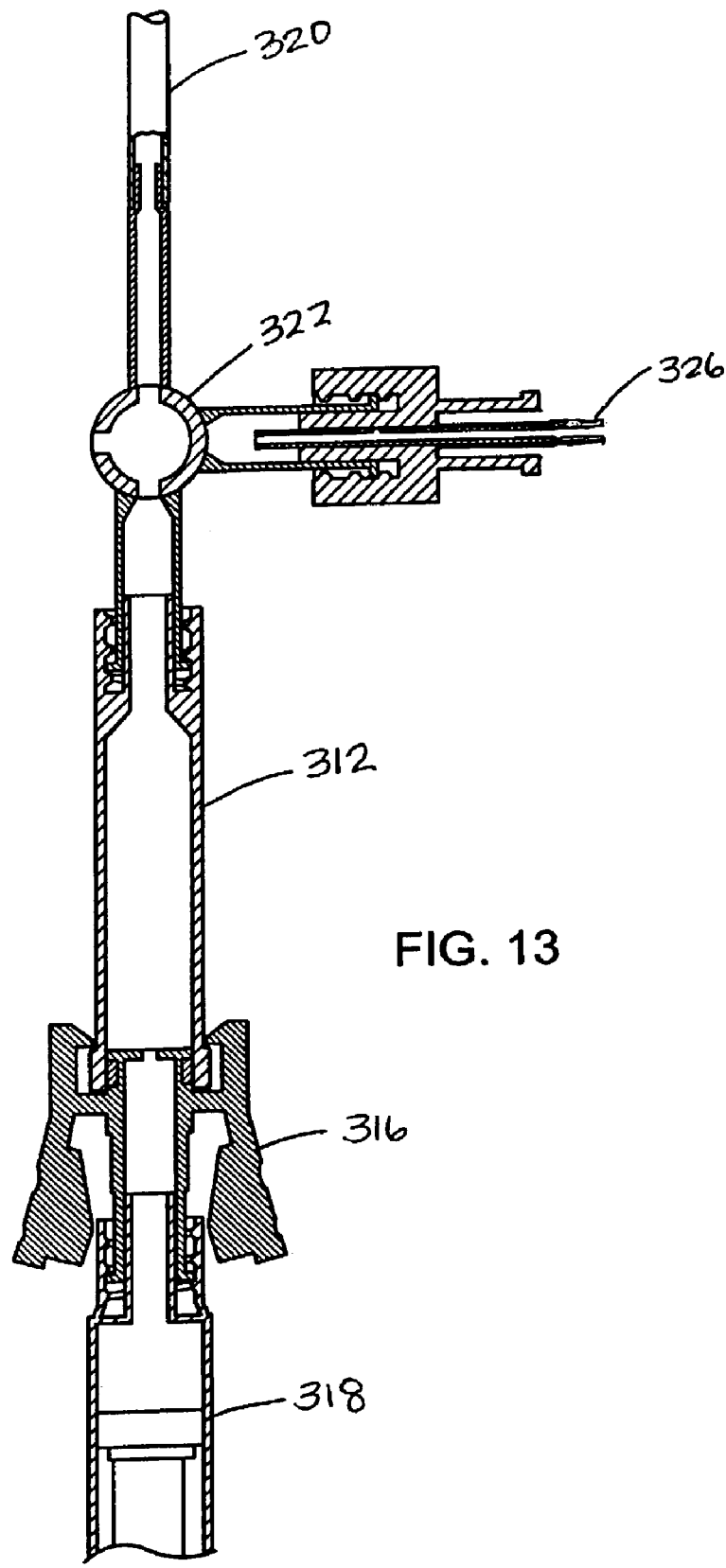
FIG. 13 is a side cross sectional view of a portion of the system of FIG. 11 including an exhaust valve, a hydration chamber, and a syringe.

As shown in the cross sectional view of FIG. 13, when the stop cock 322 is in the open delivery position, the hemostasis promoting material will pass from the hydration chamber 312 through the stop cock 322 and the side port 320 and into the introducer sheath 310 for delivery to the blood vessel puncture site.

Figure 12:
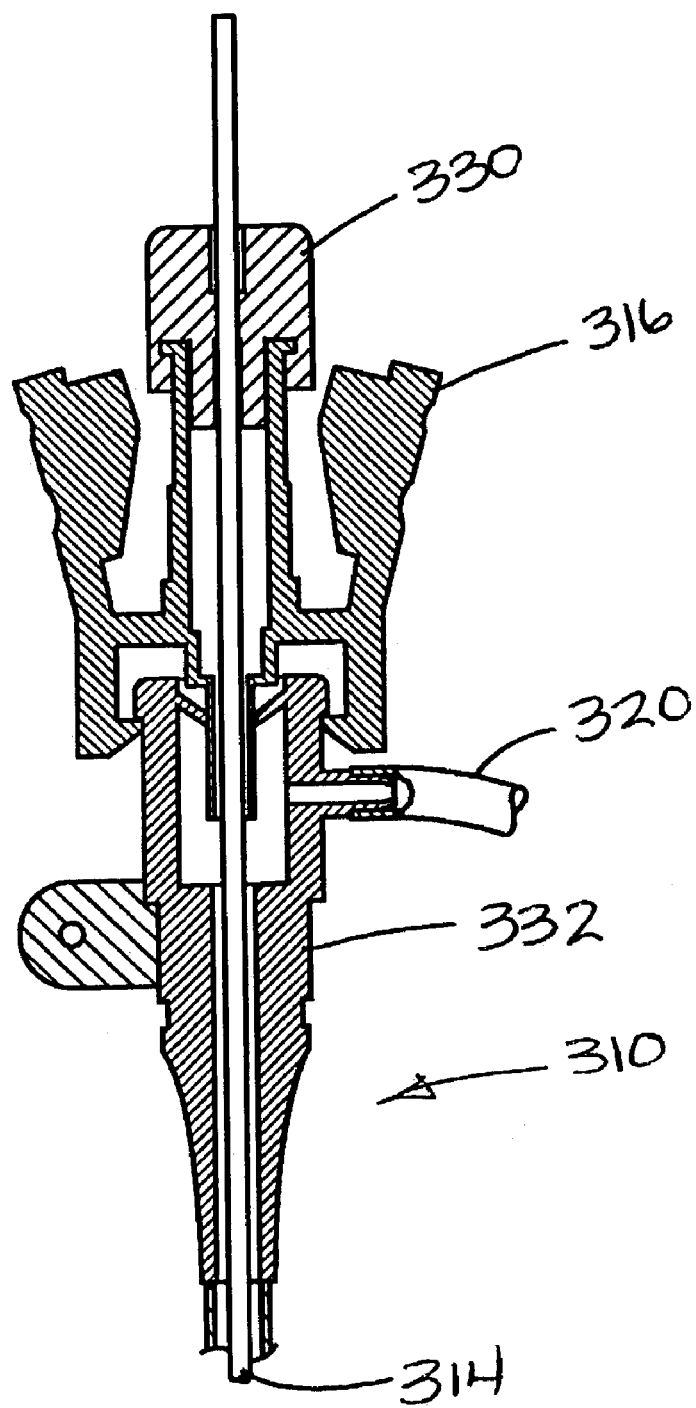
FIG. 12 is a side cross sectional view of a portion of the system of FIG. 11 including a proximal end of the introducer sheath and control tip.

FIG. 12 illustrates the connection of the control tip 314 to a proximal plug 330 which is connectable by a coupler 316 to the hub 332 of the introducer sheath 310. The hemostasis promoting material is delivered through the side port 320 of FIG. 12 and into the hub 332 of the introducer sheath 310 and then is delivered through the introducer sheath to the puncture site.

Figure 14:
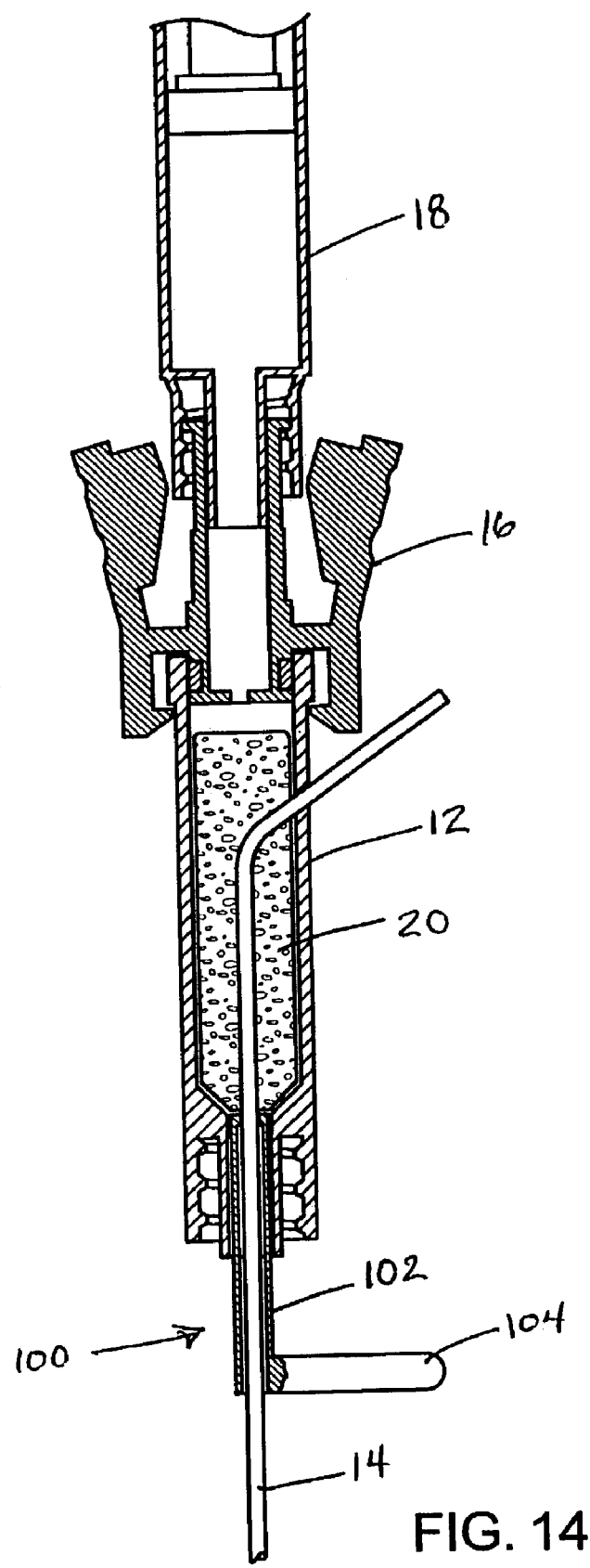
FIG. 14 is a side cross sectional view of a portion of the system of FIG. 1 with a pledget of hemostasis promoting material positioned in the hydration chamber.
Figure 15:
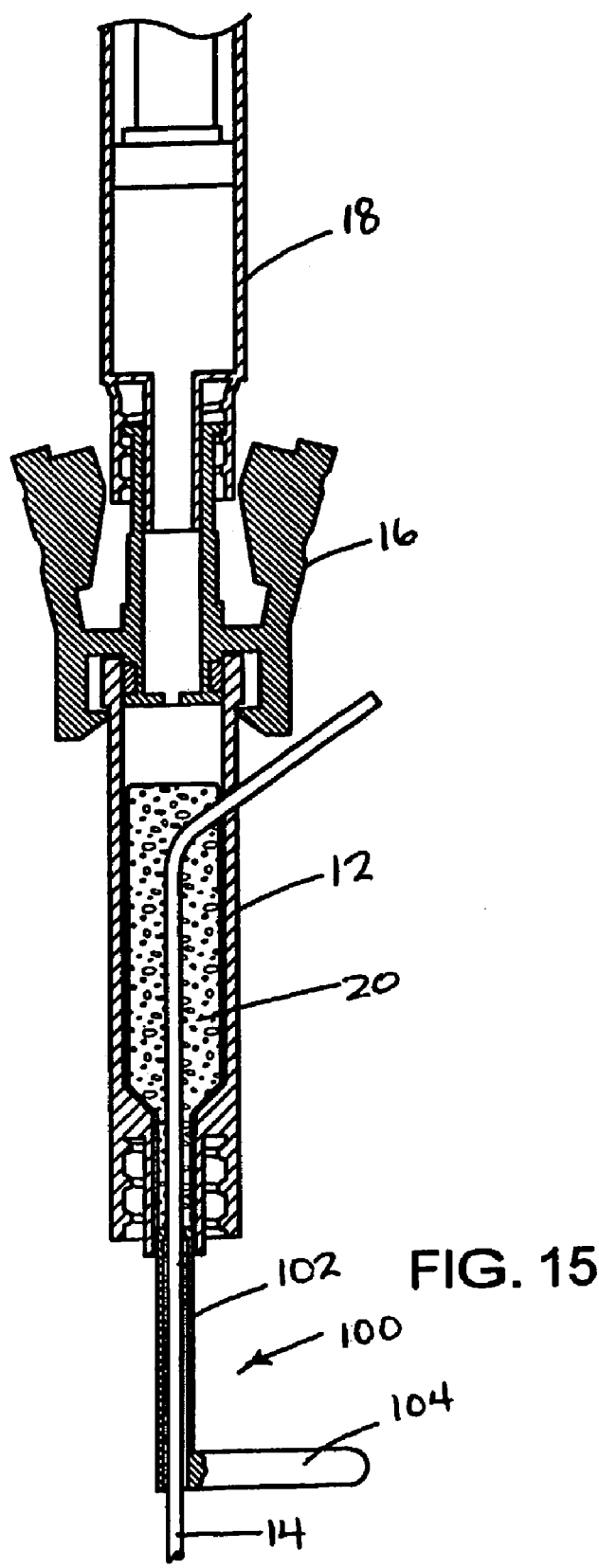
FIG. 15 is a side cross sectional view of a portion of the system of FIG. 1 with the sponge hydrated and advanced in preparation for delivery.

FIGS. 14–21 illustrate the preparation and use of the system for delivering hemostasis promoting material to a blood vessel puncture site. Although FIGS. 14–21 illustrate the procedure which is used with the embodiment of FIGS. 1–3A, a similar procedure would be used with the other embodiments described above. FIGS. 14 and 15 illustrate the hydration and staging of a pledget 20 of sponge material in the hydration chamber 12. Once the pledget 20 is inserted into the hydration chamber 12 and the coupler 16 and syringe 18 have been connected to the proximal end of the hydration chamber, the pledget is ready to be hydrated and staged. For the staging procedure a staging tube 100 is used to position a distal end of the pledget 20 and prevent the pledget from being expelled from the hydration chamber 12. The staging tube 100 includes a tube 102 having a longitudinal slit (not shown) and preferable including a handle 104. The staging tube 100 uses a longitudinal slit to allow the staging tube to be mounted onto the shaft of the control tip 14 since the staging tube 100 will not fit over the enlarged distal end 40 of the control tip. Once the staging tube 100 is placed over the shaft of the control tip 14, it is advanced into the distal end of the hydration chamber 12 to the first position shown in FIG. 14. In the position illustrated in FIG. 14 saline or other fluid is injected at high pressure into the hydration chamber 12 by the syringe 18 to hydrate the pledget 20. The staging tube 100 is then moved to the position illustrated in FIG. 15 and additional fluid is injected by the syringe 18 to advance the pledget 20 into the distal end of the hydration chamber.

It should be noted that in embodiments of the invention employing a vent tube in a hydration chamber, the pledget 20 should be staged with a distal end of the pledget positioned proximally of the inlet to the vent tube to prevent the pledget from blocking the bleed back vent. Once the pledget 20 has been hydrated and staged at a desired position in the hydration chamber 12, the hemostasis promoting material delivery system is ready to deliver the pledget to the puncture site.

Figure 16:
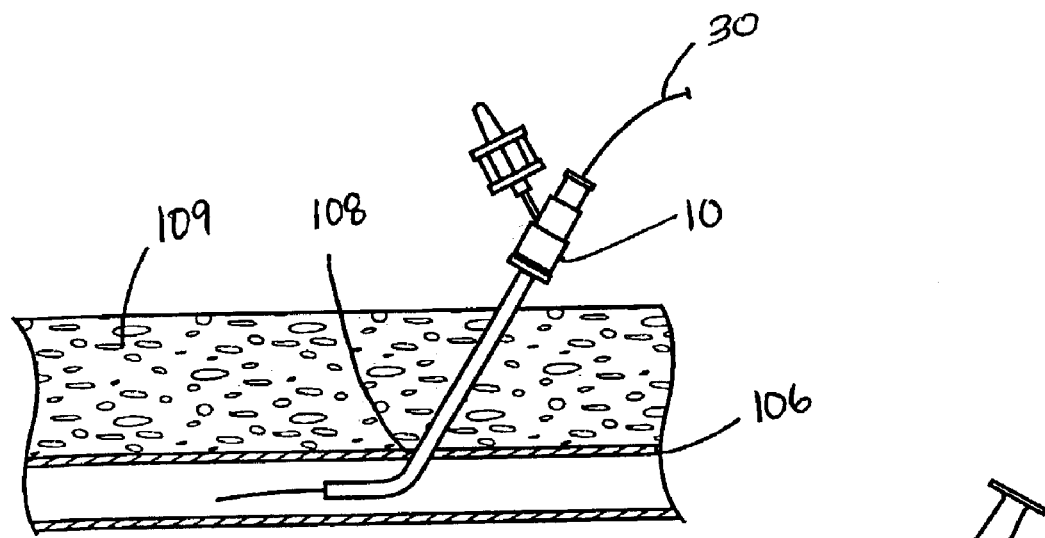
FIG. 16 is a side cross sectional view of a blood vessel puncture site with an introducer sheath and guidewire positioned in the blood vessel puncture.

FIG. 16 illustrates a blood vessel 106 with a puncture 108 and overlying tissue 109. In FIG. 16, the introducer sheath 10 and a guidewire 30 are in position in the blood vessel puncture 108 following an intravascular procedure.

Figure 17:
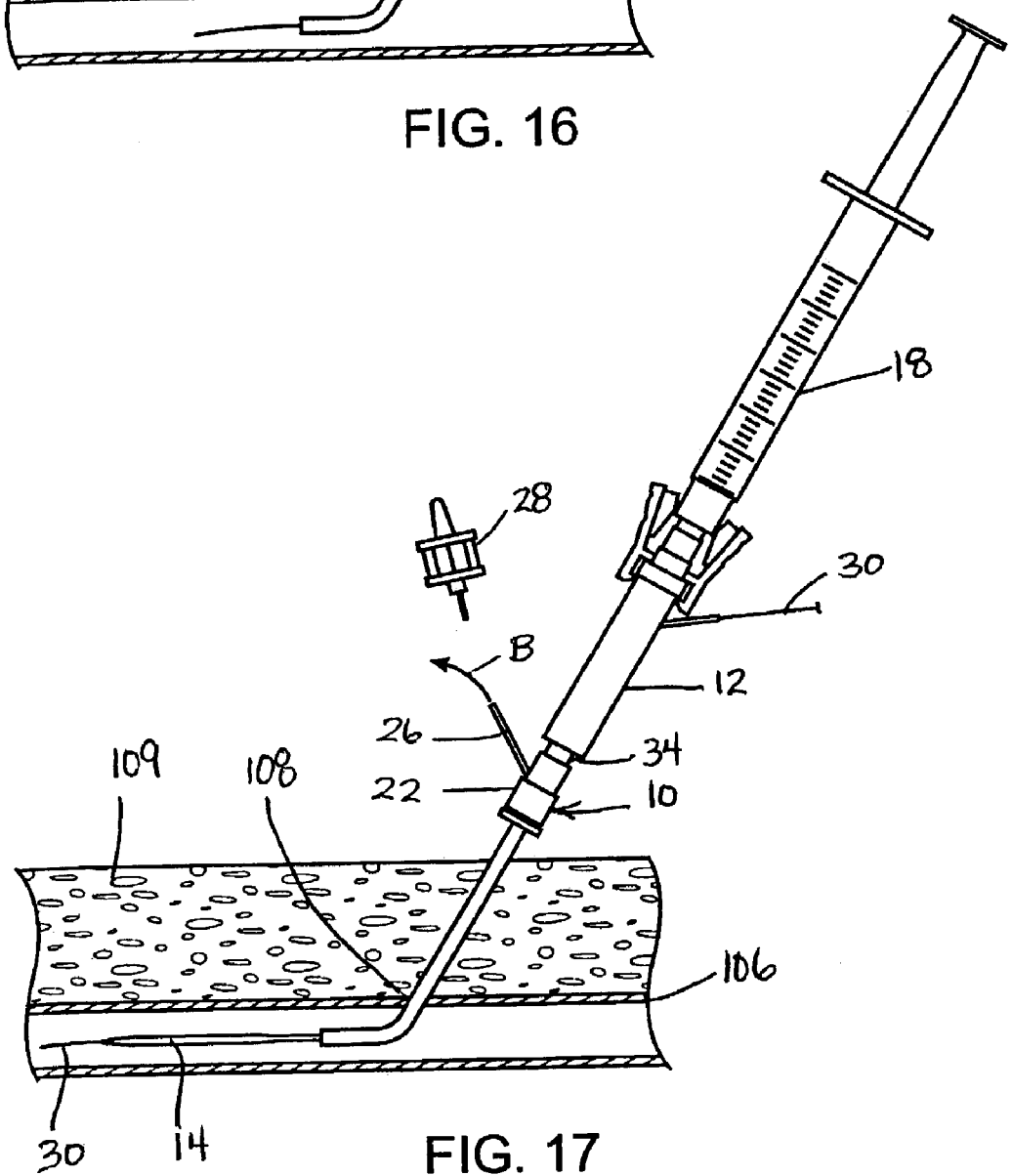
FIG. 17 is a side cross sectional view of the blood vessel puncture site with the hemostasis promoting material delivery system connected to the introducer sheath and bleed back visible from the vent tube.

In the step illustrated in FIG. 17, the control tip 14 has been inserted over the guidewire 30 and into the introducer sheath 10 and the distal end 34 of the hydration chamber 12 has been connected to the hub 22 of the introducer sheath. The vent cap 28 is then removed from vent tube 26 and the spurt of blood B called bleed back is observed from the vent tube.

Figure 18:
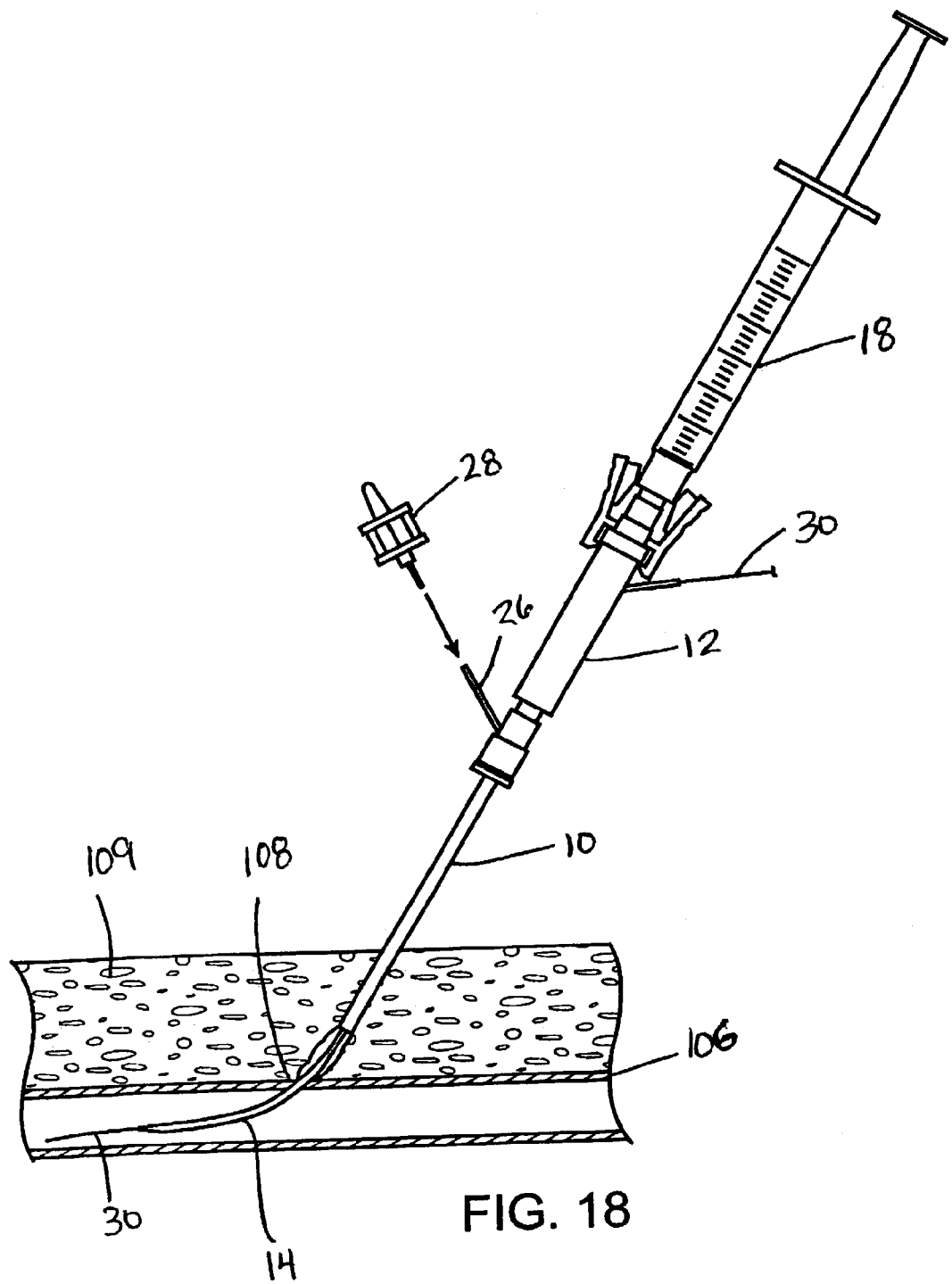
FIG. 18 is a side cross sectional view of the blood vessel puncture site with the hemostasis promoting material delivery system and introducer sheath withdrawn to a desired position for delivery of the hemostasis promoting material.

In the next step illustrated in FIG. 18, the combination of the introducer sheath 10, the hydration chamber 12, and the control tip 14, are slowly withdrawn from the puncture site until bleed back is no longer visible from the vent tube 26. When bleed back is no longer present this indicates that the enlarged distal end 40 of the control tip 14 is located in the blood vessel puncture 108 and is preventing blood from passing through the blood vessel puncture and into the introducer sheath 10.

Figure 19:
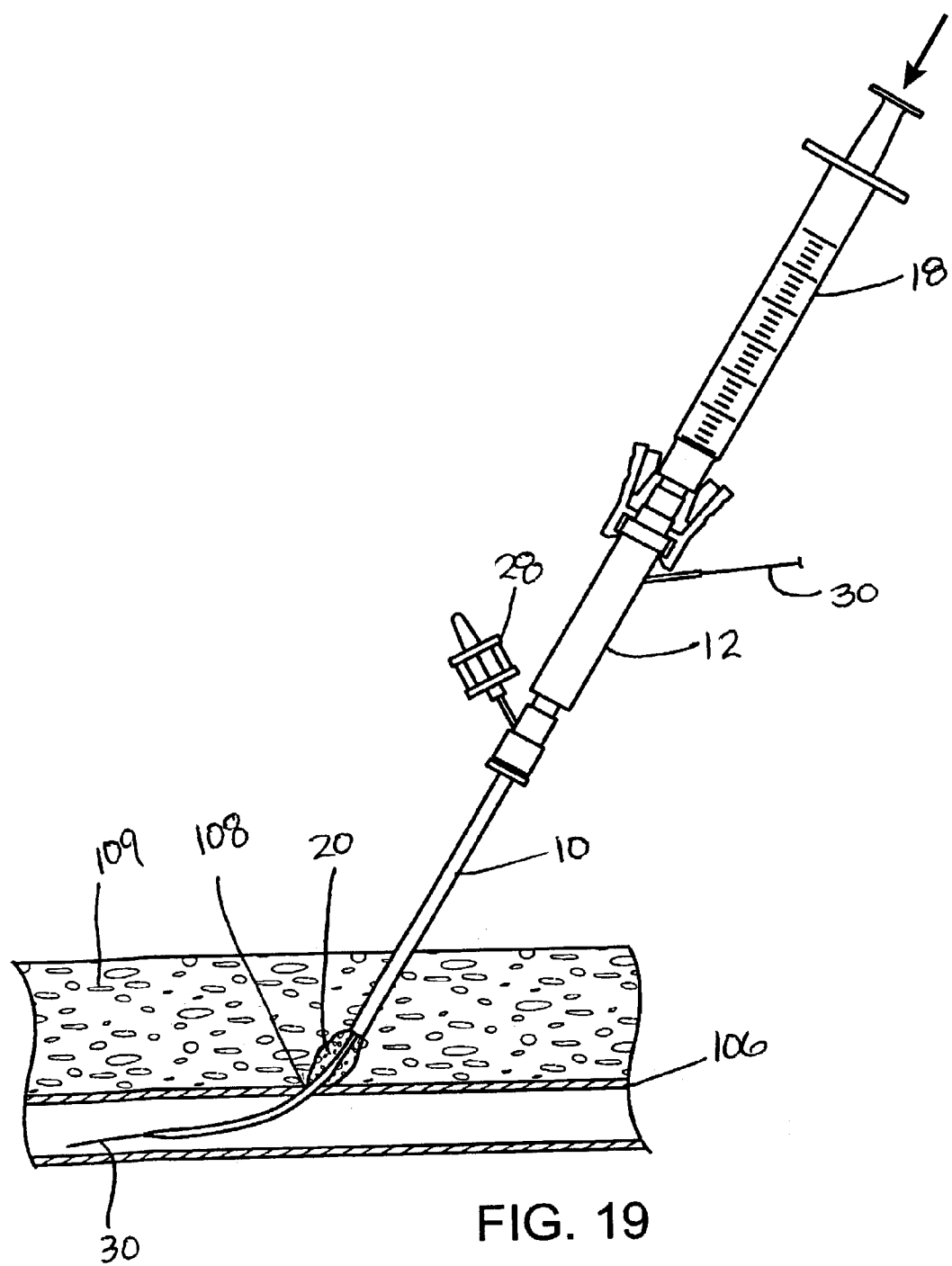
FIG. 19 is a side cross sectional view of the blood vessel puncture site with the hemostasis promoting material delivered to the blood vessel puncture site by fluid pressure.

FIG. 19 illustrates a step of injecting the hemostasis promoting material or pledget 20 to the blood vessel puncture site by fluid pressure applied by the syringe 18. The hemostasis promoting material substantially fills the tissue tract at a space between the puncture in the blood vessel and the location of a distal end of the introducer sheath 10. The pledget material, once delivered, rapidly expands to fill the tissue tract and promotes hemostasis of the blood vessel puncture.

Figure 20:
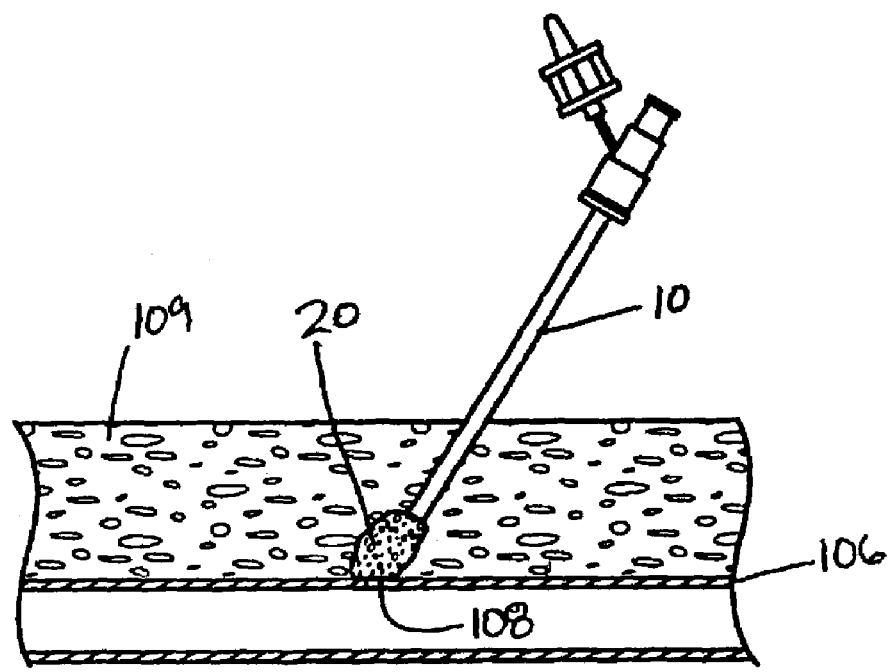
FIG. 20 is a side cross sectional view of the blood vessel puncture site with the hemostasis promoting material delivery system and guidewire removed from the introducer sheath.
Figure 21:
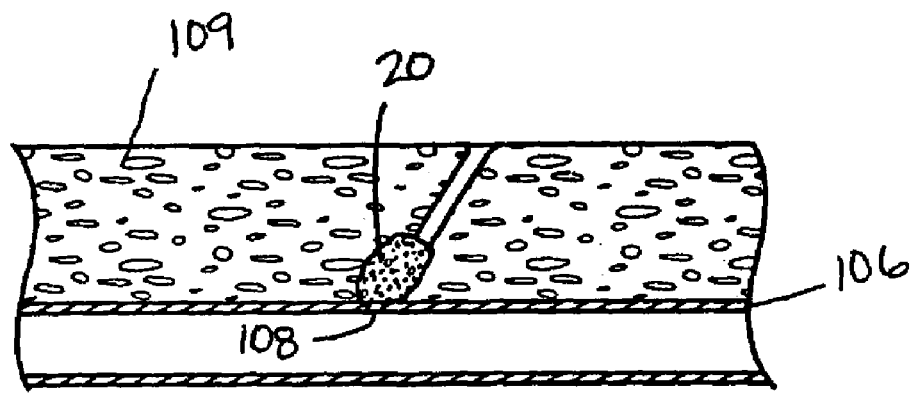
FIG. 21 is a side cross sectional view of the blood vessel puncture site with the introducer sheath withdrawn.

As shown in FIG. 20, the hydration chamber 12, the control tip 14, and the guidewire 30 are then removed from the puncture site with the introducer sheath 10 held in place to stabilize the hemostasis promoting material 20 during removal of the remaining structures. The introducer sheath 10 is then removed leaving the hemostasis promoting material in the tissue tract as shown in FIG. 21. Alternatively, the hydration chamber 12, control tip 14, guidewire 30, and introducer sheath 10 may be withdrawn together from the puncture site.

Turning now to FIGS. 22–31 there is shown an alternative embodiment wherein a pledget handling system is substituted for the hydration chamber 12 shown and described above. FIG. 22 shows the pledget handling system 400 with its proximal end coupled to the syringe 18 and the control tip extending from its distal end. The pledget handling system 400 includes a pledget chamber 402, a valve system 404 and a coupling system 406.

FIG. 23 shows the valve system 404 and the coupling system 406. The valve system 404 includes a handle 410, and the coupling system 406 includes two arms 412, and the handle 410 and arms 412 can be manipulated by a user to control the operation of the device. A bleed back tube 414 and the proximal end of the control tip 44 are also shown in this Figure.

Figure 24:
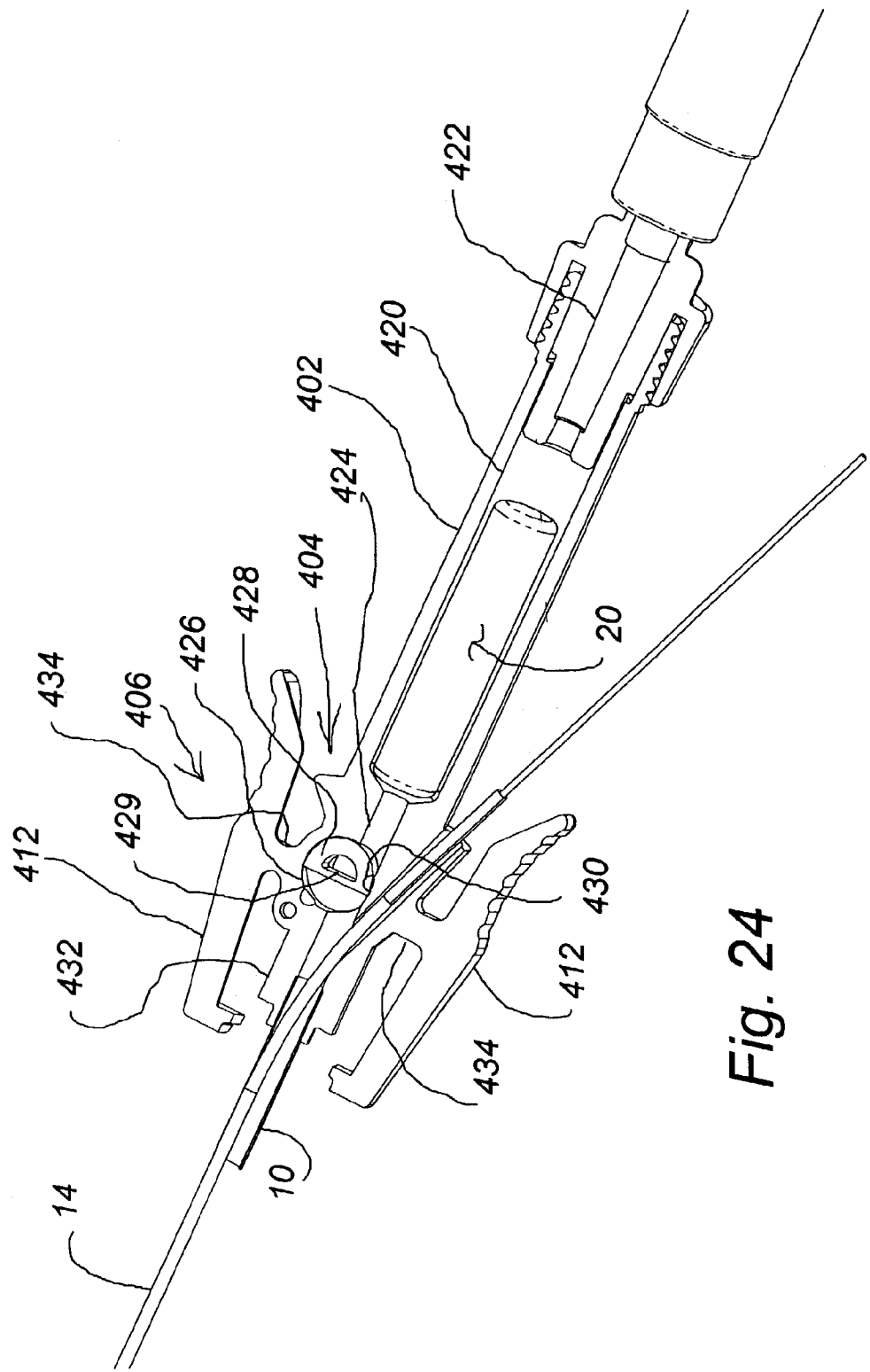
FIG. 24 is a sectional view of a portion of the device shown in FIG. 22.

FIG. 24 shows a cross section view of the pledget handling system 400, in which section lines have been omitted for the purpose of clarity. The pledget handling system 400 includes cylindrical chamber 420 connected at its proximal end to a syringe-communication cannula 422 and at its distal end to a valve-entry port 424. At the distal end of the valve-entry port 424 there is a cylindrical valve chamber 426 which contains flow-control member 428. The flow-control member 428 is essentially a truncated cylinder in configuration, having part of its distal side (in the FIG. 24 orientation) missing and also having a semi-cylindrical vent port 430 formed in its upper surface. The flow-control member 428 also has a semi-cylindrical cut-out portion 429. The flow-control member 428 is sized and shaped to be in close engagement with the valve chamber 426 so that when the flow-control member 428 is in the orientation shown in FIG. 24 fluid cannot flow from the valve-entry port 424 into the valve chamber 426. The flow-control member 428 is directly connected to the handle 410 (by a post, not shown) so that a user can rotate the flow-control member 428 by rotating the handle 410.

At its distal end the valve chamber 426 is coupled to a valve-exit port 432 which is designed to receive introducer sheath 10. The coupling system 406 includes cylindrical cannula coupler 432 and the arms 412 are connected to the body of the coupling system by posts 434 which are made of a resilient material.

Figure 25:
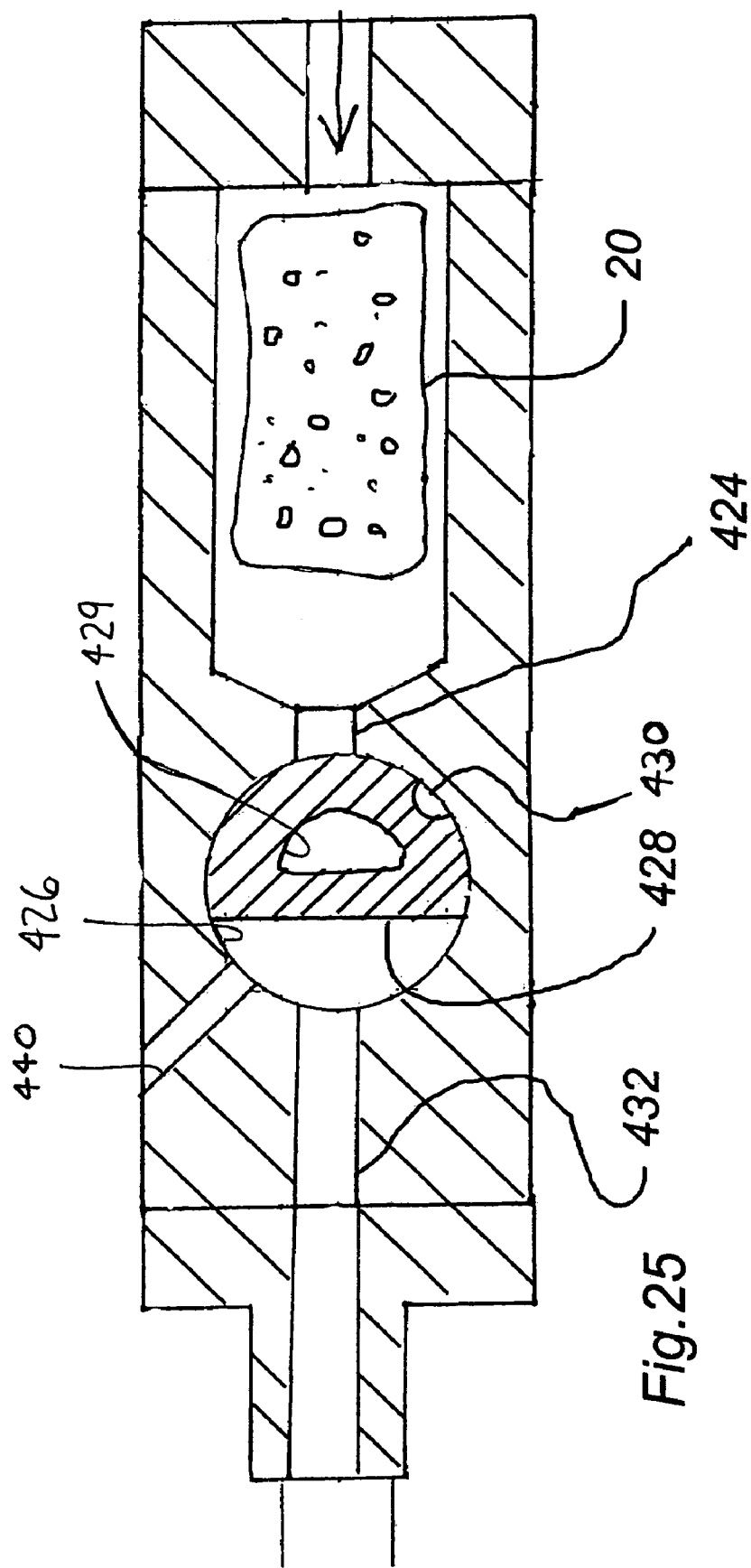
FIG. 25 is a schematic illustration of the operation of the device shown in FIG. 24.

Turning now to FIG. 25 there is a schematic illustration of the pledget handling system 400 in operation. It should be understood that the pledget 20 has been inserted into the chamber 420, the syringe and the introducer sheath 10 have been connected to the pledget handling system 400 and the device is ready for the hydrating step. The user rotates the valve arm 412 so that the flow-control member 428 is in the orientation shown in FIG. 25 so that it prevents fluid flow from the valve-entry port 424 to valve exit port 432. The user can then hydrate the pledget by operating the syringe to introduce fluid into the chamber 420.

Figure 26:
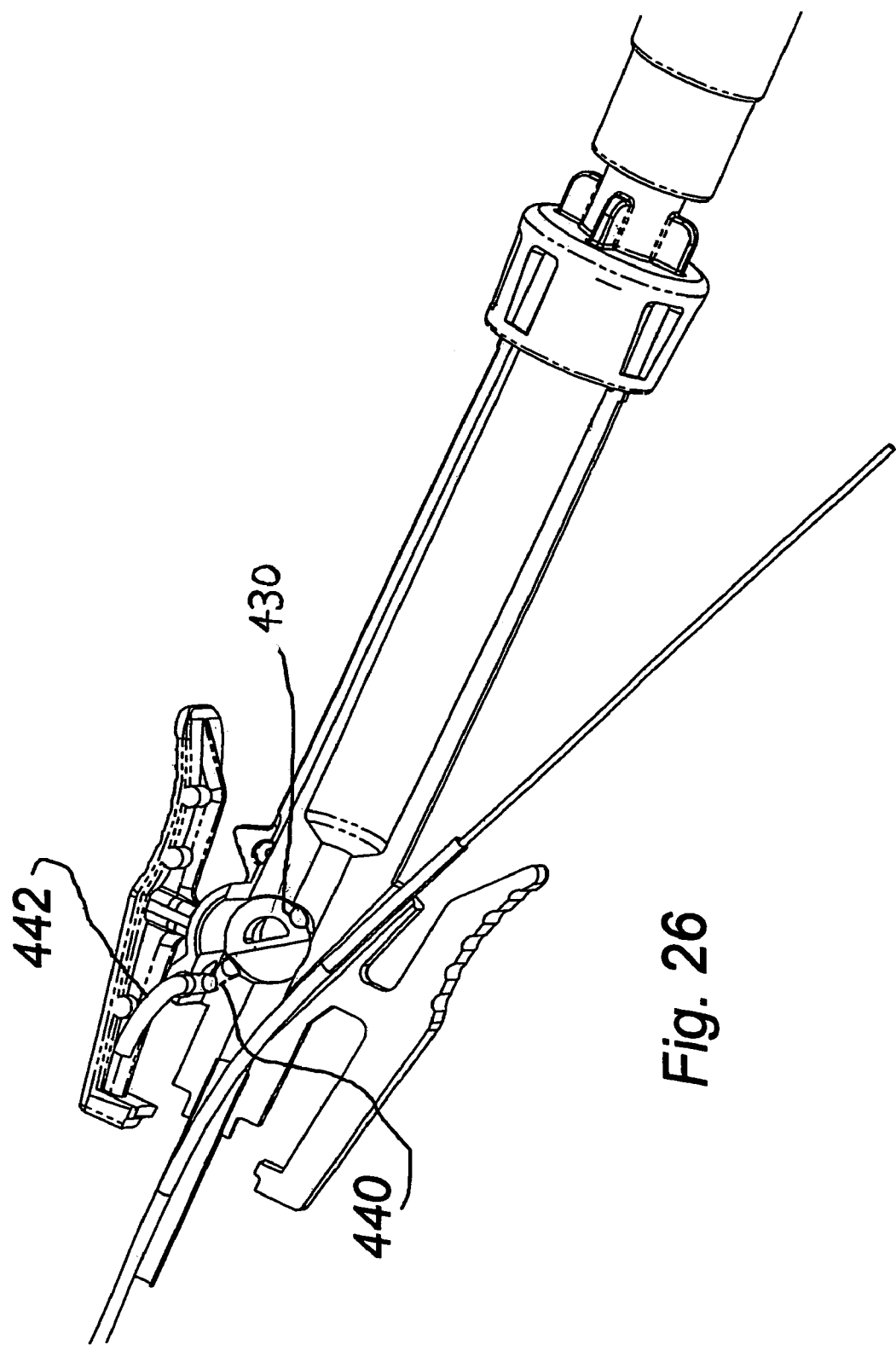
FIG. 26 is a sectional view of a portion of the device shown in FIG. 22.
Figure 27:
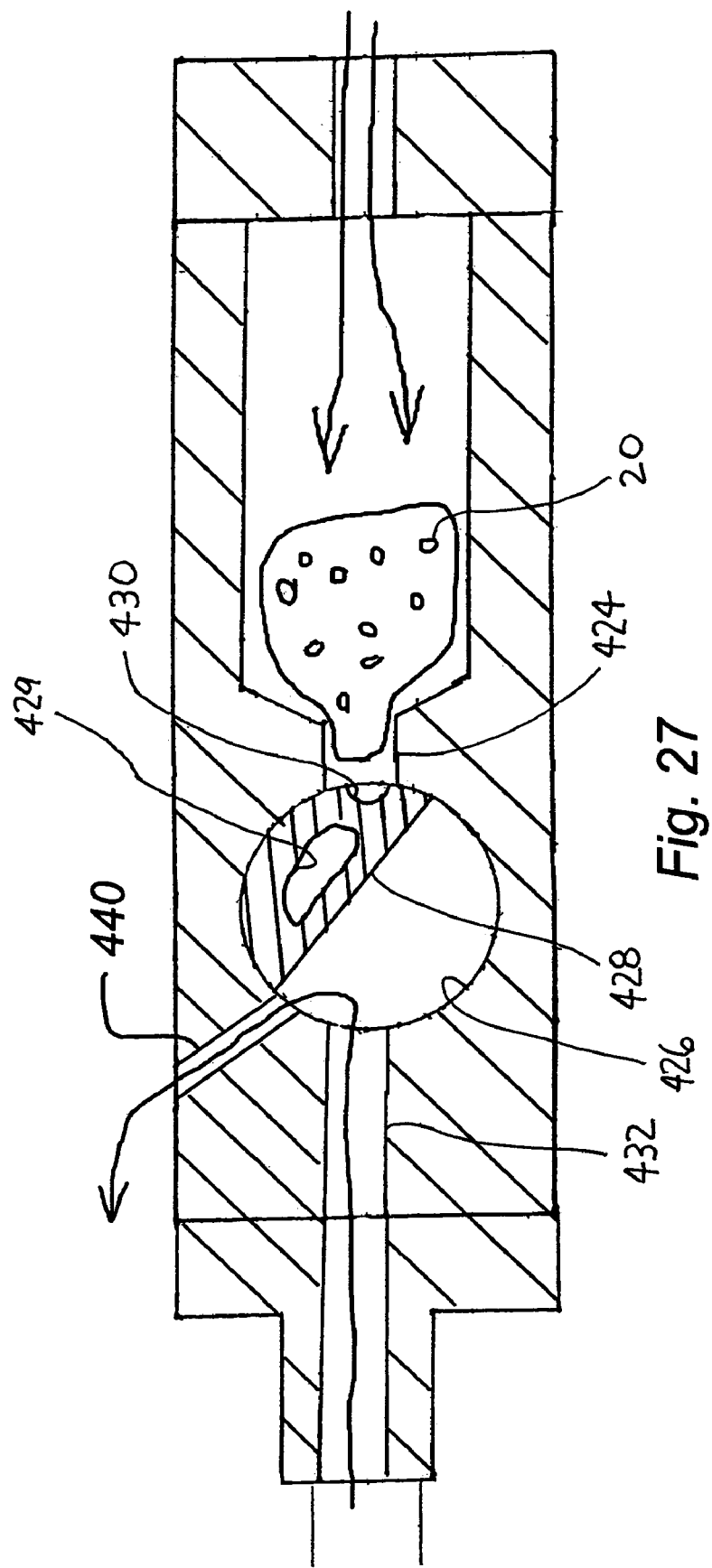
FIG. 27 is a schematic illustration of the operation of the device shown in FIG. 26.

After completing the hydrating step the user can continue to the staging step, which is illustrated in FIGS. 26 and 27. In this step the user rotates the valve arm 412 so that the flow-control member 428 is in the orientation shown in FIGS. 26 and 27. In this orientation the flow-control member 428 prevents fluid flow from flowing from the valve-entry port 424 to valve exit port 432. However, in this orientation the vent port 430 is in communication with and allows a small amount of fluid to flow from the valve-entry port 424. The vent port 430 is also in fluid-flow communication with an exit port, not shown, which extends to the outside of the pledget handling system 400, so that fluid can flow from the cut-out portion 429 to exit the pledget handling system 400. Thus, during the staging step, as best shown in FIG. 27, fluid flows through the chamber causing the pledget to travel toward the distal end of the chamber 420 while fluid flows through the exit port and out of the device at a slow rate. The cut-out portion is small in size so that it permits fluid flow but does not allow for passage of the pledget.

Also, it should be noted that a bleed back channel 440 is connected in fluid flow communication with the valve chamber 426, and a bleed back tube 442 is connected in communication with the bleed back channel 440. Thus, it can be seen that when the flow-control member is in the staging position, blood which flows through the valve exit port 432 then flows through the chamber 426 and then out of the device through bleed back tube 442. Thereby a user is given notice of bleed back. Also, the tube 442 can be rotated with respect to the pledget handling system 400 to allow the user to change the direction of the tube 442 to direct blood away from him/her self or away from others in the vicinity.

Figure 28:
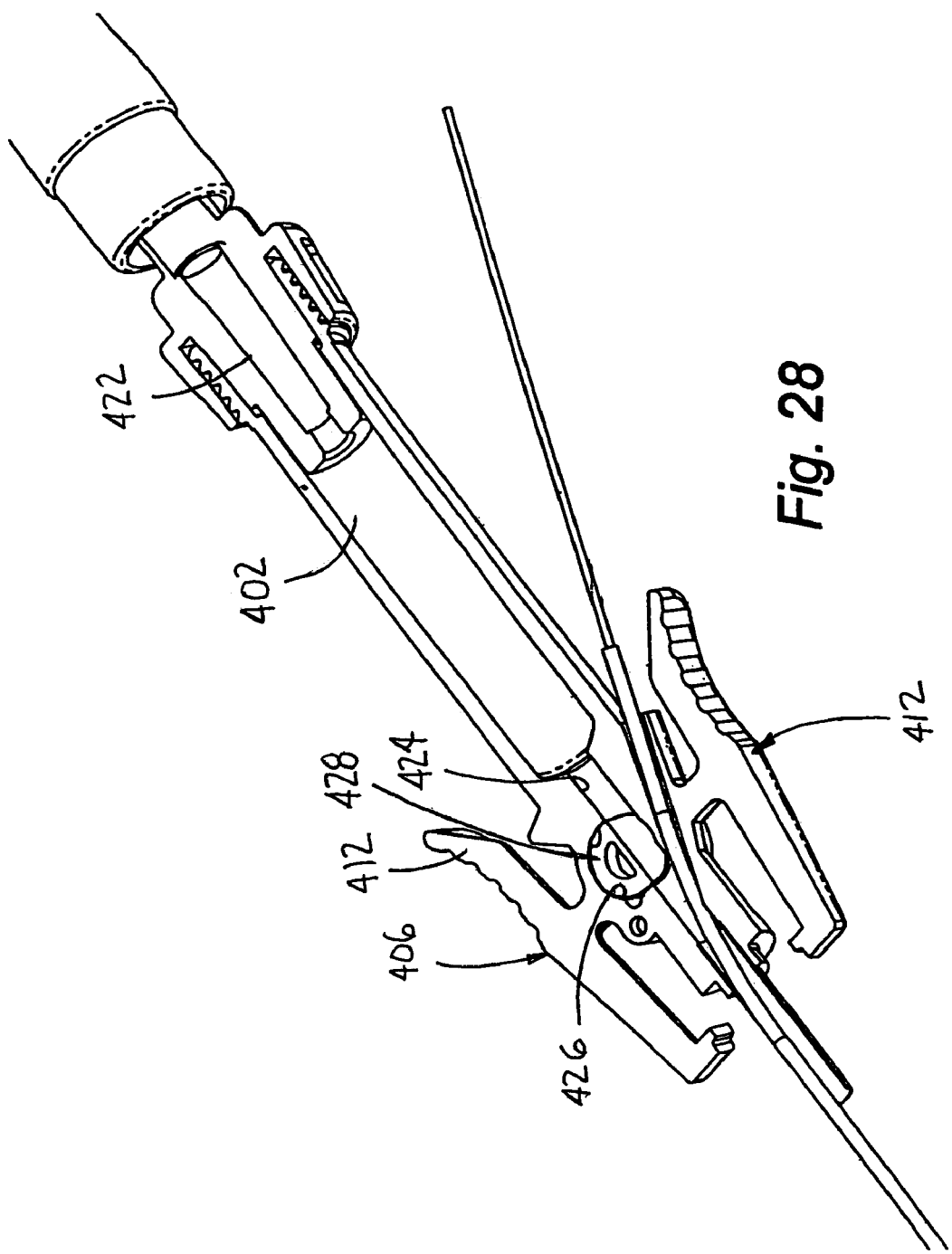
FIG. 28 is a sectional view of a portion of the device shown in FIG. 22.
Figure 29:
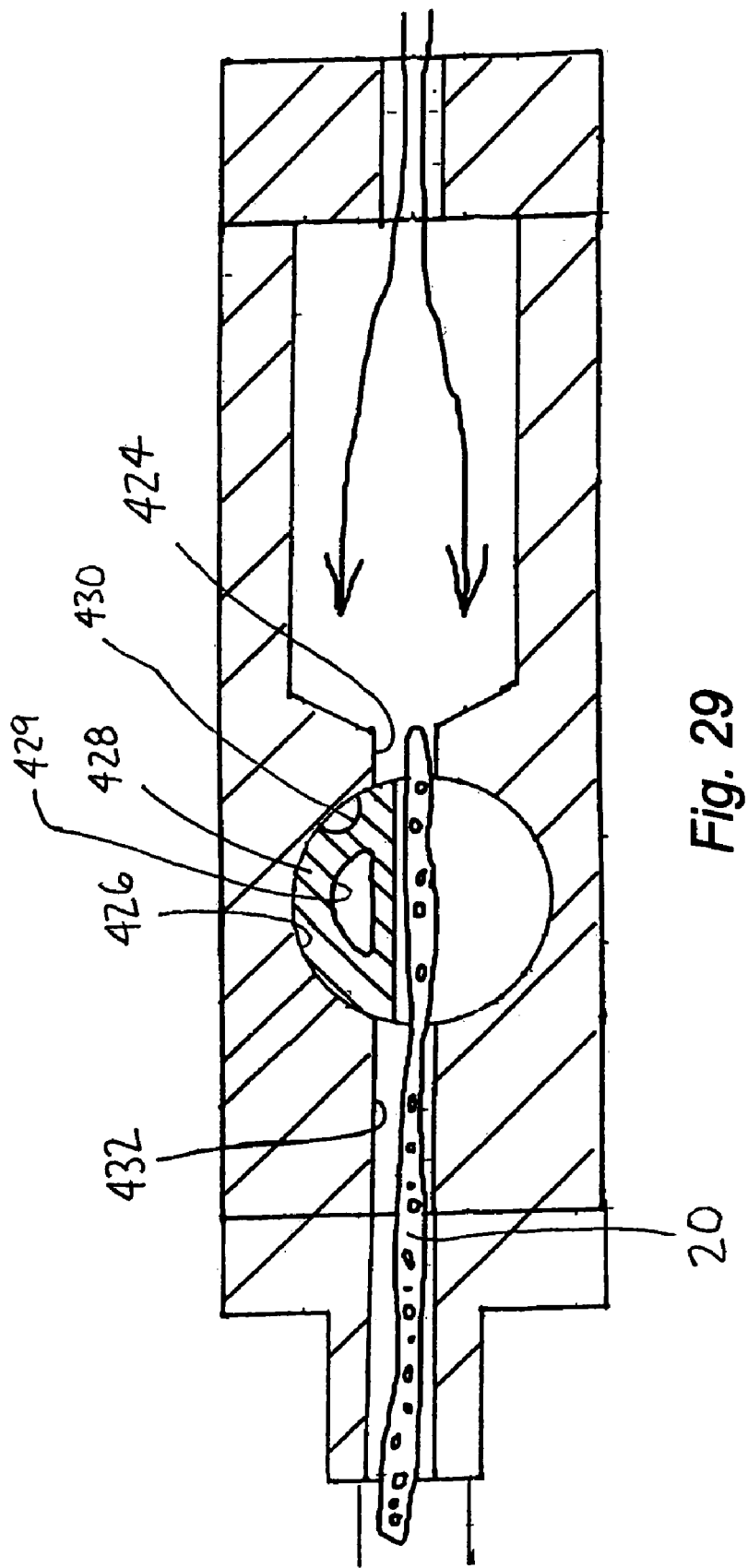
FIG. 29 is a schematic illustration of the operation of the device shown in FIG. 28.

Once the user has completed staging of the pledget, the next stage of delivery can be commenced, as shown in FIGS. 28 and 29. In the delivery step the user rotates the flow-control member to the positions as shown and applies pressure to fluid in the syringe. This causes the hydrated pledget to travel through the valve chamber 426 and then from the pledget handling system 400 and through the introducer sheath 10.

Figure 30:
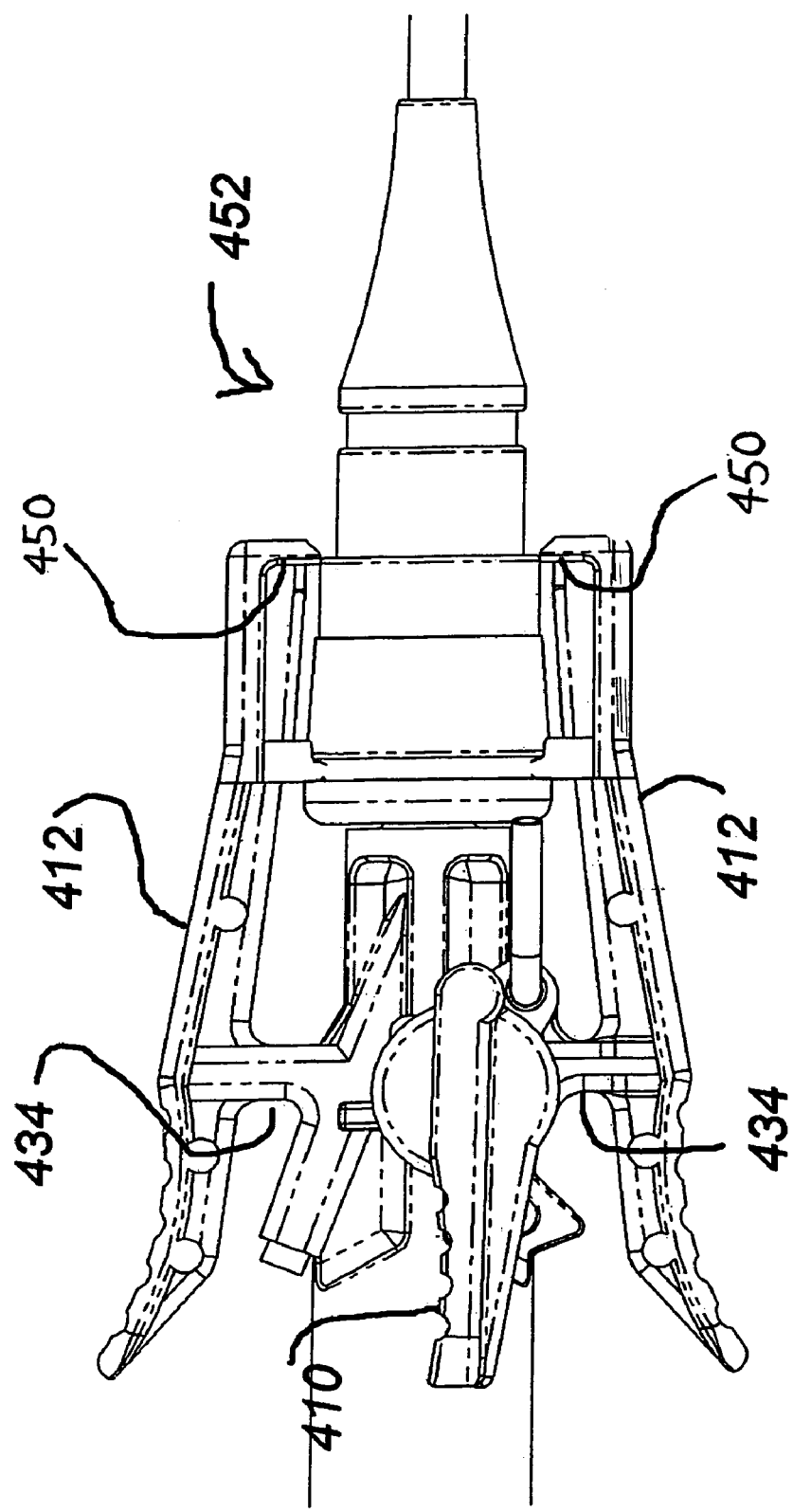
FIG. 30 is a view of an embodiment of the device shown in FIG. 28 in use with a conventional device.
Figure 31:
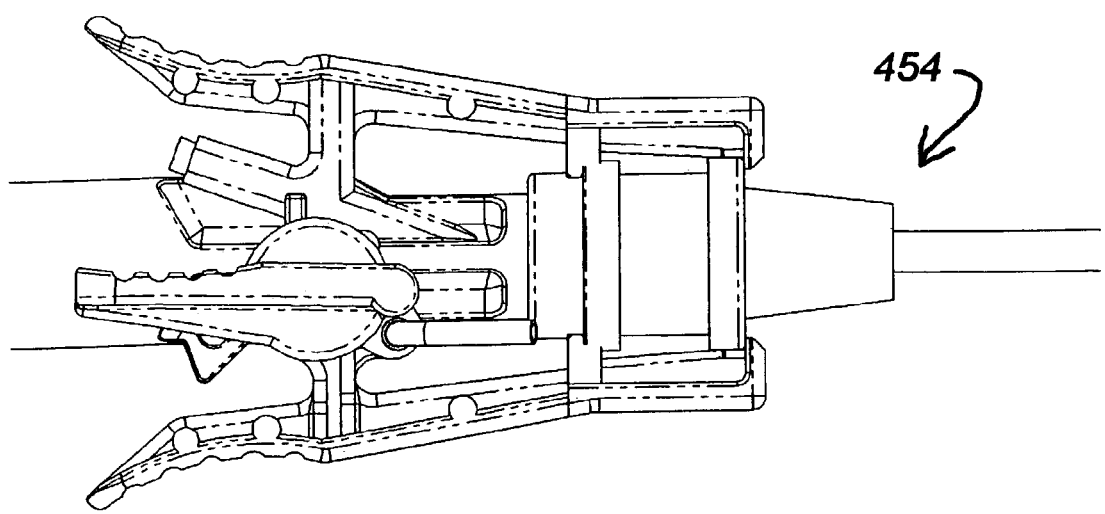
FIG. 31 is a view of an embodiment of the device shown in FIG. 28 in use with a conventional device.

Turning now to FIGS. 30 and 31, the coupling system 406 is described. The coupling system includes two arms 412, one coupled to each side of the pledget handling system 400 by posts 434. Each arm 412 has an engagement bracket 450 at its distal end. The posts are formed of resilient material so that the arms operate as levers with the posts 434 as fulcrums. Thus, to operate the coupling system the user applies pressure with the fingers to the proximate portions of the arms 412 to force them toward one another which in turn forces the engagement brackets 450 away from each other. Then the user can locate the distal end of an introducer sheath 10 between the brackets 450 and release the proximal ends of the arms 412 so that the brackets then engage the sheath 10. In FIG. 30 the coupling system is shown attached to a conventional sheath 452 made by the Terumo company. In FIG. 31 the coupling system is shown attached to a conventional sheath 454 made by the Cordis company. It can be seen that the coupling system 406 is capable of being used with a variety of conventional sheaths.

Although the present invention has been described and illustrated with bleed back provided between the introducer sheath 10 and the control tip 14, an alternative way of obtaining bleed back involves providing a hole in the control tip and bleed back through the internal lumen of the control tip. According to this alternative bleed back system, a bleed back hole is provided in the enlarged distal end 40 of the control tip 14 at a location close to the proximal end of the enlarged portion. The bleed back hole communicates with the lumen of the control tip body and allows bleed back to be viewed at the proximal end 44 of the control tip which extends out of the side wall of the hydration chamber 12.

It is preferred that the distance d between the distal end of the introducer sheath and the enlarged distal end 40 of the control tip 14 in each of the foregoing embodiments be selected so that the point at which bleed back stops is the desired delivery location for delivering the hemostasis promoting material to the blood vessel puncture. Alternatively, the introducer sheath 10, hydration chamber 12, and control tip 14 may be withdrawn an additional predetermined amount to the desired delivery location after bleed back stops.

Although the present invention has been described as a system for delivering hemostasis promoting material to a blood vessel puncture site which is delivered over a guidewire to the puncture site, the system may also be used without a guidewire in which case the lumen of the control tip may be omitted.

The entire system illustrated in the drawings may be provided in a kit or the parts may be provided individually for use with known introducer sheaths and syringes.

The hydration chamber 12 may be designed to be received interchangeably on one or more of a variety of different sheaths having different hub configurations. For example, some of the known introducer sheaths have hubs which include internal flanges, external flanges, internal threads, external threads, and/or locking detents. The hubs of some of these known sheaths are designed for connection to a correspondingly shaped dilator.

One example of a hemostasis promoting material for use in the systems of the present invention is commercially available Gelfoam from UpJohn. However, other forms of gelatin foam sponge may also be used which are modified from the commercially available Gelfoam to achieve reduced friction between the delivery system and the gelatin foam sponge. Once such modification is to change an amount of cross linking agent added to the gelatin to improve the delivery properties of the sponge.

Although the system of the present invention is particularly designed for use with an introducer sheath which has already been placed at a blood vessel puncture site, the system may also be used by removing the introducer sheath used in a procedure and replacing the procedure introducer sheath with a new introducer sheath which is connectable to the hydration chamber 12. For ease of introducing the introducer sheath and hydration chamber together, the control tip is preferably withdrawn partially into the introducer to act as a dilator for insertion of the system.

For all of the embodiments of the control tip herein, the outer diameter of the central portion of the enlarged control head is between about 5 French and about 9 French, preferable between about 6 French and about 7 French. The length of the enlarged control head, between the distal most end and the proximal end of the proximal tapered portion, is between about 1.5 inches (3.8 cm) and about 3 inches (7.6 cm), preferably between about 1.5 inches and about 2 inches (6.4 cm), and more preferably about 1.875 inches (4.8 cm). Control heads of these dimensions are well suited for controlling puncture sites as described herein, particularly puncture sites used during Seldinger-type vascular access.

The transverse cross sectional profile of all of the foregoing structures can be any desired shape, including square, oval, triangular, and preferable circular. The materials out of which the introducer sheaths, hydration chamber, control tip, and couplers are constructed are preferably selected to be relatively rigid and biocompatible, and more preferably are biocompatible polymers, biocompatible metals and metal alloys, and combinations thereof.

Figure 32:
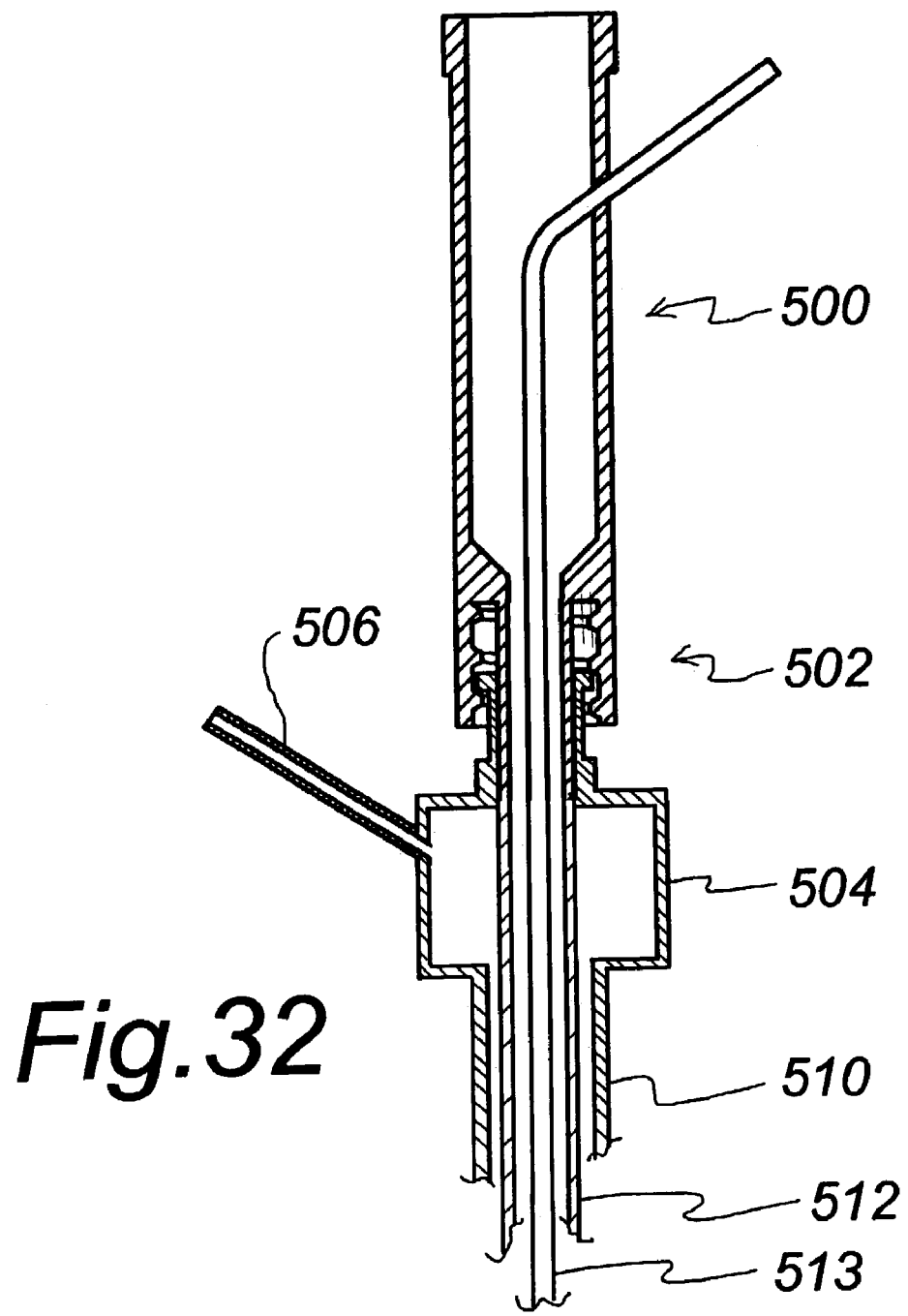
FIG. 32 is a sectional view of another embodiment.

Turning now to FIGS. 32–35 another embodiment is illustrated. In FIG. 32 hydration chamber 500 includes a coupling 502 to couple the hydration chamber 500 to a conventional introducer body 504 which includes an exhaust tube 506, and the body 504 is coupled to an introducer sheath 510 which is substantially the same as introducer sheath 10. Staging tube 512 is coupled to the distal end of the hydration chamber 500, and control tip tube 513 extends through the lumen of the introducer sheath 510.

Figure 33:
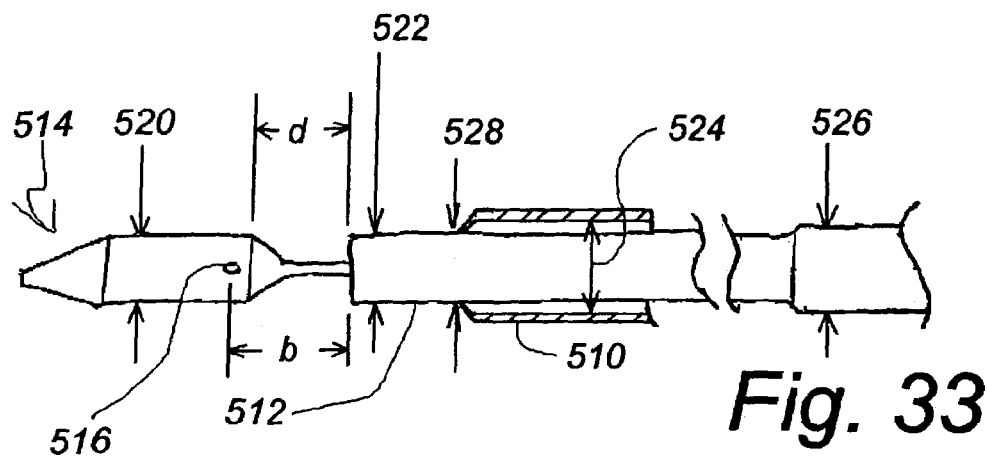
FIG. 33 is another sectional view of the embodiment of FIG. 32.

Turning to FIG. 33, the enlarged distal tip of the control tip 514, staging tube 512 and introducer sheath 510 are shown. FIG. 33 shows the distal end of the staging tube 512 which extends distally from the distal end of the sheath, and it should be noted that the distal end of the sheath 510 has a chamfer 511. The outside diameter (O.D.) 520 of the control tip and the O.D. 522 of the staging tube 512 are similar to each other and are less than the inside diameter (I.D.) 524 of the sheath such that they can extend through sheath. Alternatively, the staging tube 512 may have a second O.D. 526 larger than the O.D. 522 but equal to or less than the I.D. of the sheath at its chamfered end, i.e. the sheath minor I.D 528.

It should be understood that bleed back can be determined by a variety of methods. In the embodiment of FIGS. 32–35, the enlarged distal tip of the control tip 514 includes a bleed back port 516 which communicates with a lumen (not shown) of the control tip tube 513. When the bleed back port 516 is in the lumen of the blood vessel 106, blood flows from the vessel through the control tip tube 513 and exits the tube at its proximal end. When the introducer sheath 10, hydration chamber 12, and control tip are withdrawn together slowly from the puncture site the bleed back port 516 exits the lumen of the blood vessel 106, at which time the bleed back observed from the control tip tube 513 stops. Thus it is important that the distance "b" be known by the user so that the user can correctly position the pledget relative to the wall of the blood vessel 106.

Figure 34:
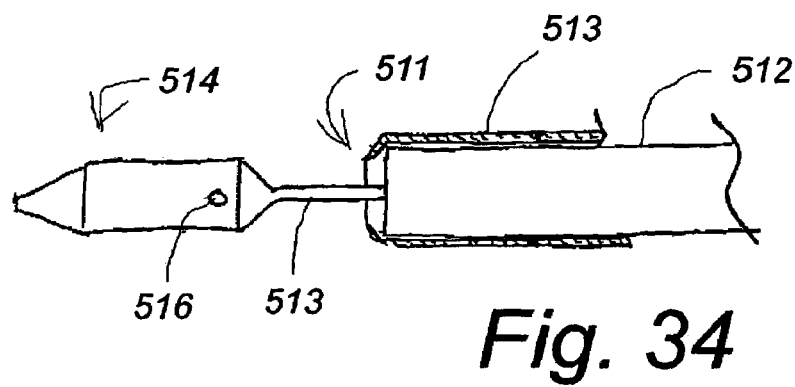
FIG. 34 is another sectional view of the embodiment of FIG. 32.

Alternatively, the introducer sheath 10, hydration chamber 12, and control tip are withdrawn together slowly from the puncture site until the bleed back observed from the vent tube 26 stops, as described above. The bleed back stops when the enlarged distal end 40 of the control tip 44 is positioned in the blood vessel puncture preventing blood from escaping from the puncture. The distance "d" between the distal end of the staging tube 512 and the proximal section of the enlarged distal tip of the control tip 514 is selected so that the point at which bleed back stops indicates that the distal end of the introducer sheath 10 is located at a desired delivery location for delivery of the hemostasis promoting material to the blood vessel puncture site. The distances "b" and "d" will be selected to correspond to the size of the pledget to be delivered to the puncture site and will be selected such that the hemostasis promoting material is located in the tissue tract adjacent the blood vessel without extending into the lumen of the blood vessel FIG. 34 shows a staging tube 512 with its distal end abutted against the sheath chamfer 511. This staging tube 512 has larger diameter than the sheath chamfer and equal to or less than the sheath I.D. 524.

Figure 35:
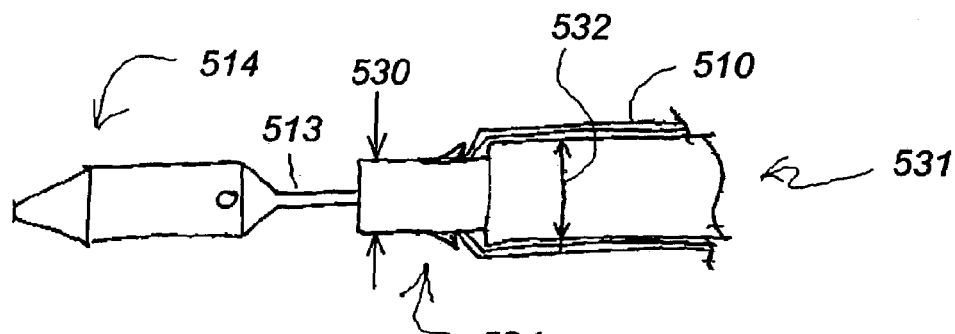
FIG. 35 is another sectional view of the embodiment of FIG. 32.

FIG. 35 shows still another embodiment of the staging tube 531. (Note that the control tip O.D. is the same as in the embodiment shown in FIG. 33.) The staging tube 531 has a first O.D. 530 for traversing sheath chamfer and a second O.D. 532 for engaging the inner surfaces of the sheath chamfer. Further, it includes sheath detents 534 to engage the distal end (or outside) of the sheath chamfer. These detents 534 may be an annular flange, tube barb, rounded or hemispherical protrusions, ramps, etc. When the user inserts the staging tube 531 into an introducer sheath 510, he pushes the staging tube 531 past the relatively light resistance of the detents 534 until he encounters the larger resistance of the second O.D. 532. The staging tube is now in a fixed position in relation to the sheath 510, facilitating manipulation of the entire assembly while maintaining the position of the staging tube 531 relative to the introducer sheath 510.

Once the user has inserted staging tube 512 or 531 into the sheath 510 and bleed back is observed, the device is withdrawn until bleed back stops. The sponge is then delivered. The user may then allow the device to dwell for some period of time. He can then remove the entire device/sheath, remove the assembly while holding the sheath stationary, or remove just the control tip while holding the staging tube stationary. After the tip is removed, the sheath can be removed.

The advantages of the embodiments shown in FIGS. 32–35 can now be appreciated. It should be understood that different manufacturers produce introducer sheaths 510 of different lengths. In the present embodiment the staging tube 512 is sufficiently long so that the distal end of the staging tube extends past the distal end of the introducer sheaths of all major manufacturers. Accordingly, distances "d" and "b" are determined by the end of the staging tube and are independent of the length of sheath 510, and a staging tube system is provided which can be used with the sheaths of different manufacturers. A further advantage is that the precision of the attachment of the introducer sheath 510 to the hydration chamber 500 is not critical.

Figure 36:
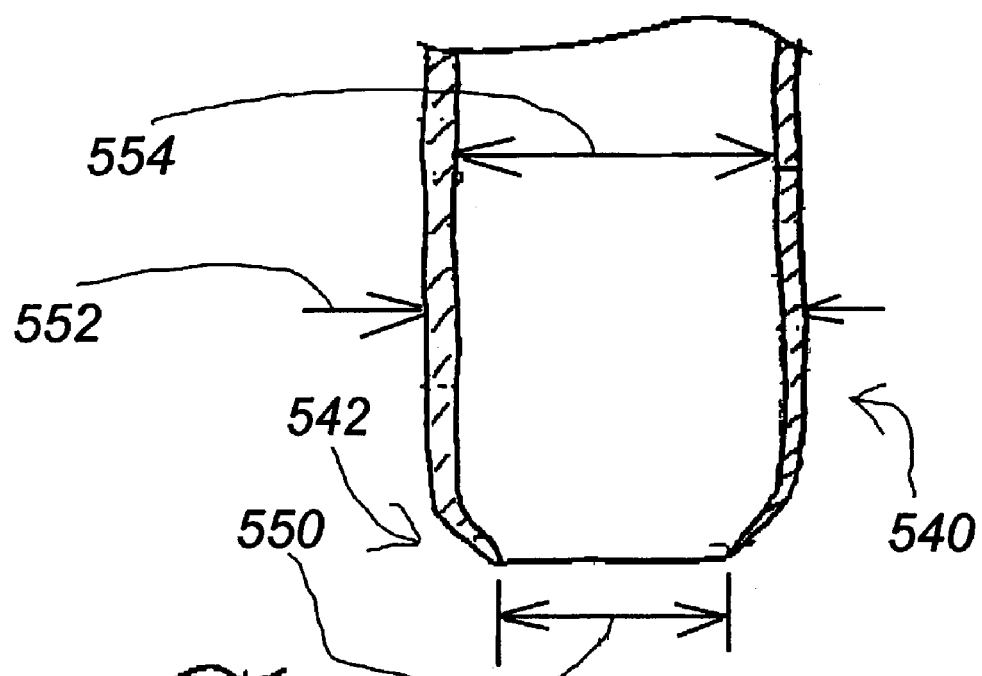
FIG. 36 is a sectional view of another embodiment.
Figure 37:
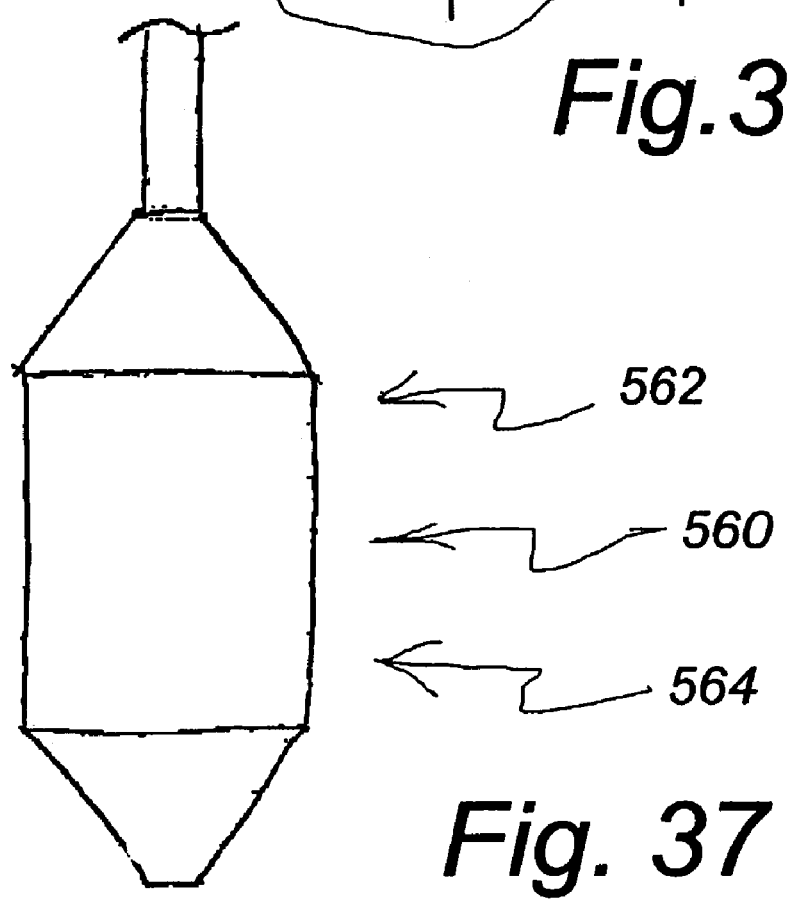
FIG. 37 is another sectional view of the embodiment of FIG. 36.

Turning to FIGS. 36 and 37, another embodiment is illustrated. In FIG. 36 the distal end of an introducer sheath 540 is shown. It should be noted that the introducer sheath has a distal taper 542, and thus the sheath has a minor inside diameter "μm" identified as 550, a major outside diameter "O" identified as 552 and a major inside diameter "M" identified as 554. With reference to FIG. 37 the enlarged distal tip of a control tip 560 is shown. The tip 560 has proximal control surface 562 with an outside diameter "p" and a distal control surface 564 with an outside diameter "d".

Sizing a control tip 560 is often optimized to reduce friction such that: O.D.p is equal to or less than "m" and O.D.d is equal to or less than "m". However, this may allow some leakage at the puncture site while the control tip control surface is in the puncture.

In the embodiment disclosed, sizing the control tip for additional control of the puncture is as follows:

O.D.p equal to or less than "M"

O.D.d equal to or less than "M"

In another preferred embodiment O.D.p "M"–epsilon (where epsilon is a small number), and O.D.d="m"–epsilon. In other words, O.D.p is a small amount less than "M" and O.D.p is a small amount less than "M". The control tip transitions somewhere along the length of the proximal and distal control surfaces from O.D.p="M"–epsilon to O.D.d="m"–epsilon. In this embodiment the control tip will "bump" past the sheath distal taper on the way in and out. It should be understood that control tips and sheaths are often made of material which can stretch without breaking, such as Teflon.

In another preferred embodiment at least a portion of the control tip control surface is equal to "O". In this case, the control tip may be assembled with the sheath ex-vivo and placed. When done, the control tip is withdrawn, splitting or stretching the sheath to allow its removal.

While the invention has been described in detail with reference to the preferred embodiments thereof, it will be apparent to one skilled in the art that various changes and modifications can be made and equivalents employed, without departing from the present invention.

What is claimed is:

1. A system for delivering hemostasis promoting material to a blood vessel puncture to facilitate hemostasis, the system comprising:
    an introducer sheath having a distal end;
    a hydration chamber coupled to said introducer sheath;
    a control tip coupled to said hydration chamber and having a distal tip adapted to locate the puncture; and,
    a staging tube having a distal end located distally of the distal end of said introducer sheath and at a predetermined distance proximally of the distal tip, the predetermined distance being sufficient for receiving the hemostasis promoting material.

2. The system of claim 1, wherein the control tip has a proximal end extending through a side of the hydration chamber between the proximal and distal ends of the hydration chamber.

3. The system of claim 1, wherein the control tip has a central lumen extending from a distal end to a proximal end of the control tip configured to receive a guidewire.

4. The system of claim 1, wherein an enlarged distal tip of the control tip extends beyond the distal end of the introducer sheath when the distal end of the hydration chamber is engaged with the proximal end of the introducer sheath.

5. The system of claim 1, wherein the hydration chamber has a first inner diameter, a second inner diameter, and a tapered portion between the first and second inner diameters for compressing the hemostasis promoting material.

6. The system of claim 5, wherein the second inner diameter is substantially the same as an inner diameter of the introducer sheath.

7. A system for delivering hemostasis promoting material to a blood vessel puncture to facilitate hemostasis, the system comprising:
    an introducer sheath having a distal end;
    a hydration chamber coupled to said introducer sheath;
    a control tip including a tube having a first diameter and an enlarged distal tip having a second diameter larger than the first diameter; and,
    a staging tube having a distal end located between the distal end of said sheath and said enlarged distal tip of the control tip.

8. A system for delivering hemostasis promoting material to a blood vessel puncture to facilitate hemostasis, the system comprising:
    an introducer sheath having a distal end;
    a hydration chamber configured to receive and hydrate a pledget of hemostasis promoting material, the hydration chamber having a distal end configured to be connected to the proximal end of the introducer sheath and a proximal end configured to be connected to a syringe;
    a control tip including a tube having a first diameter and an enlarged distal tip having a second diameter larger than the first diameter, the tube configured to extend from an interior of the hydration chamber through the distal end of the hydration chamber, through the introducer, and out the distal end of the introducer; and,
    a staging tube having a distal end located between said distal end of said sheath and said enlarged distal tip of the control tip.

9. A system for delivering hemostasis promoting material to a blood vessel puncture to facilitate hemostasis, the system comprising:
    an introducer sheath having a distal end, said introducer sheath having a distal taper so that the introducer sheath has a first inside diameter proximal of said distal taper and a second inside diameter at said distal taper;
    a hydration chamber coupled to said introducer sheath; and,
    a control tip coupled to said hydration chamber, wherein the diameter of said control tip is greater than the second inside diameter.

10. A process for delivering hemostasis promoting material to a blood vessel puncture to facilitate hemostasis, using an introducer sheath having a distal end and a staging tube having a distal end, the process comprising:
    locating a puncture locator at a predetermined distance distally with respect to the staging tube distal end;
    locating the distal end of said staging tube distally of the distal end of said introducer sheath; and,
    delivering the hemostasis promoting material through said introducer sheath and staging tube after the puncture locator has located the puncture.

* * * * *